(12) United States Patent
Nakashima et al.

(10) Patent No.: US 7,312,278 B2
(45) Date of Patent: Dec. 25, 2007

(54) WATER-ABSORBING AGENT AND PRODUCTION PROCESS THEREFOR, AND SANITARY MATERIAL

(75) Inventors: Yasuhisa Nakashima, Himeji (JP); Hiroyuki Ikeuchi, Himeji (JP); Yasuhiro Fujita, Himeji (JP); Makoto Nagasawa, Himeji (JP); Shigeru Sakamoto, Himeji (JP); Yorimichi Dairoku, Himeji (JP); Katsuyuki Wada, Himeji (JP); Shinichi Fujino, Himeji (JP); Toshimasa Kitayama, Himeji (JP); Kazuhisa Hitomi, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 612 days.

(21) Appl. No.: 10/333,614

(22) PCT Filed: Jun. 7, 2002

(86) PCT No.: PCT/JP02/05642

§ 371 (c)(1),
(2), (4) Date: Jan. 22, 2003

(87) PCT Pub. No.: WO02/100451

PCT Pub. Date: Dec. 19, 2002

(65) Prior Publication Data

US 2004/0106745 A1 Jun. 3, 2004

(51) Int. Cl.
*C08L 33/02* (2006.01)
*C08L 63/00* (2006.01)

(52) U.S. Cl. .............. 525/119; 525/329.5; 525/329.7; 525/384

(58) Field of Classification Search ............... 525/119, 525/329.5, 329.7, 384
See application file for complete search history.

(56) References Cited

U.S. PATENT DOCUMENTS

| | | | |
|---|---|---|---|
| 4,043,952 A | 8/1977 | Ganslaw et al. | |
| 4,051,086 A | 9/1977 | Reid | |
| 4,587,308 A | 5/1986 | Makita et al. | |
| 4,666,983 A | 5/1987 | Tsubakimoto et al. | |
| 4,734,478 A | 3/1988 | Tsubakimoto et al. | |
| RE32,649 E | 4/1988 | Brandt et al. | |
| 4,755,560 A | 7/1988 | Ito et al. | |
| 4,771,105 A | 9/1988 | Shirai et al. | |
| 5,164,459 A | 11/1992 | Kimura et al. | |
| 5,322,896 A | 6/1994 | Ueda et al. | |
| 5,409,771 A | 4/1995 | Dahmen et al. | |
| 5,610,208 A | 3/1997 | Dairoku et al. | |
| 5,610,220 A | 3/1997 | Klimmek et al. | |
| 6,071,976 A | 6/2000 | Dairoku et al. | |
| 6,187,872 B1 * | 2/2001 | Yanase et al. | 525/330.2 |
| 6,265,488 B1 * | 7/2001 | Fujino et al. | 525/119 |
| 6,297,319 B1 * | 10/2001 | Nagasuna et al. | 525/96 |
| 6,297,335 B1 | 10/2001 | Funk et al. | |
| 6,414,214 B1 | 7/2002 | Engelhardt et al. | |
| 6,809,158 B2 * | 10/2004 | Ikeuchi et al. | 525/375 |

FOREIGN PATENT DOCUMENTS

| | | |
|---|---|---|
| DE | 40 20 780 | 8/1991 |
| EP | 0 668 080 | 8/1995 |
| EP | 0 761 241 | 3/1997 |
| EP | 0 349 240 | 4/1997 |
| EP | 0 827 753 | 3/1998 |
| EP | 0 856 528 | 8/1998 |
| EP | 0 882 502 | 12/1998 |
| EP | 0 940 148 | 9/1999 |
| EP | 0 940 149 | 9/1999 |
| EP | 1 019 886 A2 | 8/2000 |
| EP | 1 029 886 A2 * | 8/2000 |
| JP | 52-117393 | 10/1977 |
| JP | 51-136588 | 11/1977 |
| JP | 58-180233 | 10/1983 |
| JP | 59-189103 | 10/1984 |
| JP | 60-163956 | 8/1985 |
| JP | 60-255814 | 12/1985 |
| JP | 61-16903 | 1/1986 |
| JP | 61-211305 | 9/1986 |
| JP | 61-252212 | 11/1986 |
| JP | 61-257235 | 11/1986 |
| JP | 61-264006 | 11/1986 |
| JP | 62-7745 | 1/1987 |
| JP | 1-292004 | 11/1989 |

(Continued)

Primary Examiner—Robert D. Harlan
(74) Attorney, Agent, or Firm—Roylance, Abrams, Berdo & Goodman, L.L.P.

(57) ABSTRACT

There is provided: a production process for a water-absorbing agent having stable properties in a short time; and a water-absorbing agent. The production process comprises the step of blending an acid-group-containing water-absorbent resin powder with a noncrosslinkable water-soluble inorganic base and/or an irreducible alkaline-metal-salt pH buffer and further with a dehydratable crosslinking agent reactable with the acid group, thereby subjecting the resin powder to crosslinking treatment, or comprises the step of blending an acid-group-containing water-absorbent resin powder with the above base and/or pH buffer and further with a crosslinking agent reactable with the acid group, thereby subjecting the resin powder to crosslinking treatment, wherein the resin powder has a weight-average particle diameter of 300 to 600 μm wherein the ratio of fine powders having particle diameters of not larger than 150 μm in the resin powder is not more than 10 weight %.

18 Claims, 3 Drawing Sheets

FOREIGN PATENT DOCUMENTS

| | | |
|---|---|---|
| JP | 2-153903 | 6/1990 |
| JP | 3-126730 | 5/1991 |
| JP | 3-179008 | 8/1991 |
| JP | 4-106108 | 4/1992 |
| JP | 6-15574 | 3/1994 |
| JP | 6-74331 | 9/1994 |
| JP | 6-298841 | 10/1994 |
| JP | 7-33818 | 2/1995 |
| JP | 07-088171 | 4/1995 |
| JP | 7-278225 | 10/1995 |
| JP | 09-235378 | 9/1997 |
| JP | 10-101735 | 4/1998 |
| JP | 10-244151 | 9/1998 |
| JP | 11-315216 | 11/1999 |
| JP | 11-349625 | 12/1999 |
| JP | 2000-026510 | 1/2000 |
| JP | 2000-197818 | 7/2000 |
| JP | 2002-504566 | 2/2002 |
| JP | 2002-504597 | 2/2002 |
| WO | WO 94/15651 | 7/1994 |
| WO | WO 95/26209 | 10/1995 |
| WO | WO 97/25013 | 7/1997 |
| WO | WO 98/49441 | 11/1998 |
| WO | WO 99/42494 | 8/1999 |
| WO | WO 99/43720 | 9/1999 |
| WO | WO 00/31153 | 6/2000 |
| WO | WO 00/53644 | 9/2000 |
| WO | WO 00/53664 | 9/2000 |
| WO | WO 01/74913 | 10/2001 |
| WO | WO 02/20068 | 3/2002 |
| WO | WO 02/22717 | 3/2002 |

\* cited by examiner

WATER-ABSORBING AGENT AND PRODUCTION PROCESS THEREFOR, AND SANITARY MATERIAL

TECHNICAL FIELD

The present invention relates a water-absorbing agent and a production process therefor. More particularly, the present invention relates to: a water-absorbing agent, which is obtained by modifying a water-absorbent resin with a crosslinking agent, and displays a high absorption capacity both without load and under a load, and further a high saline flow conductivity; and a production process therefor.

BACKGROUND ART

In recent years, water-absorbent resins are widely used as constituent materials of sanitary materials, such as disposable diapers, sanitary napkins, and so-called incontinent pads, for the purpose of causing the water-absorbent resins to absorb body fluids.

Examples of the above water-absorbent resins include: crosslinked products of partially neutralized polyacrylic acids; hydrolyzed products of starch-acrylic acid graft polymers; saponified products of vinyl acetate-acrylic acid ester copolymers; hydrolyzed products of acrylonitrile- or acrylamide copolymers, or crosslinked products of these hydrolyzed products; and crosslinked polymers of cationic monomers.

Hitherto, it has been said that the above water-absorbent resins should have properties such as excellent absorption amount of liquid, absorption rate, gel strength, gel liquid permeability, and suction force to suck up water from a base material containing aqueous liquids, when they are in contact with aqueous liquids such as body fluids. Then, various water-absorbent resins (water-absorbing agents), combing at least two of these properties and displaying excellent performance (absorption properties) when they are used for sanitary materials (e.g. disposable diapers and sanitary napkins), has been proposed hitherto.

For example, as to a method for improving absorption properties (e.g. absorption capacity without load and absorption capacity under a load) of a water-absorbent resin in good balance, there is a known art in which the surface neighborhood of the water-absorbent resin is crosslinked, and then various methods have been disclosed.

Known examples thereof include methods in which the following materials are used: polyhydric alcohols (JP-A-180233/1983 and JP-A-016903/1986); polyglycidyl compounds, polyaziridine compounds, polyamine compounds, or polyisocyanate compounds (JP-A-189103/1984); glyoxal (JP-A-117393/1977); polyvalent metals (JP-A-136588/1976, JP-A-257235/1986 and JP-A-007745/1987); silane coupling agents (JP-A-211305/1986, JP-A-252212/1986, and JP-A-264006/1986); alkylene carbonates (DE 4020780); polyvalent heterocyclic carbonates (JP-A-315216/1999); oxazolidinones (WO 99/42494); polyvalent oxazolidinones (WO 99/43720); oxadines (WO 00/31153); and oxazoline compounds (JP-A-197818/2000).

And further, when the improvement of the absorption properties is carried out by the above crosslinking agents, there are also known methods in which additives (e.g. inert blending promoters, acid catalysts, and bases) are used in order to further improve the performance. That is to say, known examples of the methods (1) in which the inert blending promoters are used as the additives include methods in which the following materials are allowed to exist: inert inorganic powders (JP-A-163956/1985 and JP-A-255814/1985); water containing salts and/or hydroxides of polyvalent metals (JP-A-007745/1987); dihydric alcohols (JP-A-292004/1989); water together with ether compounds (JP-A-153903/1990); water-soluble polymers (JP-A-126730/1991); alkylene oxide adducts of monohydric alcohols, monovalent salts of organic acids or lactams (JP-B-074331/1994 and JP-A-033818/1995); monovalent metal salts (WO 98/49221); and cations (WO 00/53664 and WO 00/53644).

Furthermore, known examples of the methods (2) in which the acid catalysts are used as the additives include methods in which the following materials are allowed to exist: phosphoric acid (WO 94/15651); and inorganic acids or organic acids (JP-A-278225/1995).

In addition, known examples of the method (3) in which the bases are used as the additives include a method in which water-soluble alkaline compounds are allowed to exist (JP-A-298841/1994).

Because these additives, as used in the above methods (1), (2), and (3), exist together with the crosslinking agent, the balance of the absorption properties of the water-absorbing agent can also be improved to a certain extent in comparison with the case that the crosslinking agent exists alone. However, it was yet still difficult to say that the balance was sufficient.

Specifically, as to the additives (inert blending promoters) as used in the above method (1), the effect is caused by acting as blending promoters when the water-absorbent resin as used contains fine powders in a large amount. On the other hand, because of their existence, there were problems such that: almost no improvement of the absorption properties is observed, for example, because the absorptivity of the crosslinking agent to a water-absorbent resin powder is excessively lowered or because the crosslinking reaction is inhibited; and even if the improvement is achieved, it is necessary to increase the amount of the crosslinking agent as used, to prolong the reaction time, and to raise the reaction temperature.

As to the additives (acid catalysts) as used in the above method (2), the effect as a catalyst that promotes the reaction of the crosslinking agent can be expected. However, when the amount to obtain a certain effect is added, the pH of a crosslinking agent solution is extremely lowered and, especially in such as cases of water-absorbent resins of a partially neutralized type containing an acid group, the acidification of the surface is caused, so that the control of the absorptivity of the crosslinking agent is difficult. In addition, there are disadvantages in that: the acidification of the surface increases the adhesion between the water-absorbent resin particles, and it tends to form aggregates. As a result, there are problems such that: the desired crosslinking density of the water-absorbent resin particle surface layer cannot be obtained; and it is difficult to obtain what displays satisfactory performance.

As to the above method (3), there is disclosed the surface-crosslinking which is carried out by combination of the additives (bases) with compounds having at least two functional groups easily reactable with a carboxyl group (e.g. multivalent metal salts, polyepoxy compounds, polyaziridinyl compounds, and polyisocyanate compounds), and the improvement of the gel strength and absorption capacity under a comparatively light load (20 g/cm$^2$) are intended. However, in the method as described in JP-A-298841/1994, the improvement of the blendability of the surface-crosslinking agent or the properties of the water-absorbent resin is still insufficient. Particularly, it was difficult to improve an SFC and an absorption capacity (AAP) under a heavy load (4.83 kPa, about 50 g/cm$^2$) (both are mentioned below.), as requested in recent years.

In addition, examples of typical water-absorbent resins include acrylic water-absorbent resins comprised of crosslinked products of partially neutralized acrylic acid salts, from the viewpoint of high properties and costs. Then, as to production processes for such acrylic water-absorbent resins, the following two methods are generally carried out: a method which involves polymerizing acrylic acid and its salt as neutralized to a predetermined neutralization ratio beforehand (hereinafter, referred to as neutralization polymerization method); and a method which involves polymerizing unneutralized or low neutralized acrylic acid; and thereafter post-neutralizing the resultant polymer gel (hereinafter, referred to as acid-type polymerization method).

In comparison with the neutralization polymerization method, the latter acid-type polymerization method tends to obtain a water-absorbent resin having a high absorption capacity and a low extractable content. However, it takes plenty of time to uniformly neutralize a crosslinked hydrogel polymer after polymerization, and further the neutralization is technically very difficult, and there are cases where the neutralization ratios of individual particles of the resultant water-absorbent resin powder are non-uniform among those particles. JP-A-010173/1998 (EP 0882502 A1) discloses that: in this case, although the water-absorbent resin of the acid-type polymerization method has a high absorption capacity and a low extractable content, and even if the surface-crosslinking treatment is carried out, the performance of the water-absorbing agent is not sufficiently obtained.

That is to say, when water-absorbent resins are surface-crosslinked, there has hitherto been a case where the necessary surface-crosslinking treatment is different depending upon the difference of the neutralization ratio, therefore the desired performance of the water-absorbing agent is not obtained at other neutralization ratio even if the optimum crosslinking treatment for a certain neutralization ratio is carried out. Particularly, when the neutralization ratios of the individual particles of the water-absorbent resin powder are various, there has hitherto been a case where the desired performance of the water-absorbing agent is not be obtained.

As is mentioned above, the surface-crosslinking treatment cannot be uniformly carried out by the prior arts. As a result, the balance of various properties (such as a CRC, AAP, and SFC as mentioned below, particularly SFC) of the water-absorbent resin as obtained went bad, and further the scatter of the SFC was caused. Therefore, for example, the scatter of properties of diapers among lots and the great difference of properties even in one diaper were caused.

DISCLOSURE OF THE INVENTION

Object of the Invention

The present invention has been made in consideration of the above prior art problems. That is to say, an object of the present invention is to provide: a process for producing a water-absorbing agent; which process involves, in the crosslinking treatment step, the use of an additive that displays effects as a blending promoter but never inhibits a crosslinking reaction and, according to circumstances, further has effects as a reaction catalyst, and which process can achieve uniform surface-crosslinking almost regardless of the difference in neutralization ratio of a water-absorbent resin resultant from partial-neutralization polymerization and almost regardless of the uniformity of the neutralization ratio resultant from the post-neutralization operation after the acid-type polymerization. Furthermore, the object of the present invention is also to provide: a process for producing a water-absorbing agent in a short time; and a water-absorbing agent; which process can give a water-absorbing agent that is excellent in balance of absorption capacity without load, absorption capacity under load, and saline flow conductivity and further exhibits so little scatter of the saline flow conductivity values among lots or in each lot during the production as to have stable properties.

SUMMARY OF THE INVENTION

The present inventors diligently studied a water-absorbing agent having excellent absorption properties. As a result, they found out that the above problems are solved by using a specific additive together with a specific crosslinking agent of the water-absorbent resin, and the present invention has been completed.

That is to say, a water-absorbing agent, according to the present invention, relates to a water-absorbing agent which is a particulate water-absorbing agent of which the major proportion is comprised of a water-absorbent resin that is obtained by a process including the step of polymerizing an unsaturated monomer component and has a crosslinked structure, with the water-absorbing agent being characterized in that: the particulate water-absorbing agent includes particles having particle diameters of smaller than 850 μm but not smaller than 150 μm in a ratio of not less than 90 weight % of all particles of the particulate water-absorbing agent; and includes at least two members selected from the group consisting of: particles (A1) having particle diameters of smaller than 850 μm but not smaller than 600 μm; particles (A2) having particle diameters of smaller than 600 μm but not smaller than 500 μm; particles (A3) having particle diameters of smaller than 500 μm but not smaller than 300 μm; and particles (A4) having particle diameters of smaller than 300 μm but not smaller than 150 μm; and further satisfies the following properties:

a 30 minutes' absorption capacity of not less than 31 g/g without load for a 0.90 weight % physiological saline (CRC);

a 60 minutes' absorption capacity of not less than 24 g/g under a load of 4.83 kPa for a 0.90 weight % physiological saline (AAP);

a saline flow conductivity of not less than 20 (unit: $10^{-7} \times cm^3 \times s \times g^{-1}$) for a 0.69 weight % physiological saline (SFC); and an SFC variation index of 0 to 25% wherein the SFC variation index is defined by the following equation (1):

SFC variation index (%)=[(standard deviation of SFCs of particles $A1$ to $A4$)/(SFC of entire particulate water-absorbing agent)]×100　　(1)

In addition, another water-absorbing agent, according to the present invention, relates to a water-absorbing agent which is a particulate water-absorbing agent of which the major proportion is comprised of a water-absorbent resin that is obtained by a process including the step of polymerizing an unsaturated monomer component and has a crosslinked structure, with the water-absorbing agent being characterized in that: the particulate water-absorbing agent includes particles having particle diameters of smaller than 850 μm but not smaller than 150 μm in a ratio of not less than 90 weight % of all particles of the particulate water-absorbing agent; and includes at least two members selected from the group consisting of: particles (A1) having particle diameters of smaller than 850 μm but not smaller than 600 μm; particles (A2) having particle diameters of smaller than 600 μm but not smaller than 500 μm; particles (A3) having particle diameters of smaller than 500 μm but not smaller than 300 μm; and particles (A4) having particle diameters of smaller than 300 μm but not smaller than 150 μm; and further satisfies the following properties:

a 30 minutes' absorption capacity of not less than 31 g/g without load for a 0.90 weight % physiological saline (CRC);

a 60 minutes' absorption capacity of not less than 24 g/g under a load of 4.83 kPa for a 0.90 weight % physiological saline (AAP);

a saline flow conductivity of not less than 20 (unit: $10^{-7} \times cm^3 \times s \times g^{-1}$) for a 0.69 weight % physiological saline (SFC); and an SFC variation coefficient of 0 to 0.25, wherein the SFC variation coefficient is defined by the following equation (2):

SFC variation coefficient=(standard deviation of SFCs of particles $A1$ to $A4$)/(average of SFCs of particles $A1$ to $A4$)     (2).

Furthermore, yet another water-absorbing agent, according to the present invention, relates to a continuously produced water-absorbing agent which is a particulate water-absorbing agent of which the major proportion is comprised of a water-absorbent resin that is obtained by a process including the step of polymerizing an unsaturated monomer component and has a crosslinked structure, with the water-absorbing agent being characterized in that: the particulate water-absorbing agent includes particles having particle diameters of smaller than 850 μm but not smaller than 150 μm in a ratio of not less than 90 weight % of all particles of the particulate water-absorbing agent; and includes at least two members selected from the group consisting of: particles (A1) having particle diameters of smaller than 850 μm but not smaller than 600 μm; particles (A2) having particle diameters of smaller than 600 μm but not smaller than 500 μm; particles (A3) having particle diameters of smaller than 500 μm but not smaller than 300 μm; and particles (A4) having particle diameters of smaller than 300 μm but not smaller than 150 μm; and further satisfies the following properties:

a 30 minutes' absorption capacity of not less than 31 g/g without load for a 0.90 weight % physiological saline (CRC);

a 60 minutes' absorption capacity of not less than 24 g/g under a load of 4.83 kPa for a 0.90 weight % physiological saline (AAP);

a saline flow conductivity of not less than 20 (unit: $10^{-7} \times cm^3 \times s \times g^{-1}$) for a 0.69 weight % physiological saline (SFC); and an SFC standard deviation of not more than 5.0 in a continuous production system, wherein the SFC standard deviation in a continuous production system is defined by the following equation (4):

SFC standard deviation in a continuous production system=standard deviation of SFC of each lot     (4)

where: the CRC, AAP, and SFC are on average of the lots; each lot has a weight of not less than 20 kg; and the number of the lots is not smaller than 10.

Furthermore, yet another water-absorbing agent, according to the present invention, is a particulate water-absorbing agent obtained by a process including the steps of: polymerizing a monomer including an acid-group-containing monomer (salt); and then post-neutralizing the resultant polymer; and then surface-crosslinking the resultant water-absorbent resin, wherein the particulate water-absorbing agent or the water-absorbent resin has a neutralization index of not less than 15 and exhibits a 60 minutes' absorption capacity of not less than 20 g/g under a load of 4.83 kPa for a 0.90 weight % physiological saline (AAP) after the surface-crosslinking.

In addition, a production process for a water-absorbing agent, according to the present invention, is characterized by comprising the step of blending a water-absorbent resin powder (a) with a noncrosslinkable water-soluble inorganic base (b1) and/or an irreducible alkaline-metal-salt pH buffer (b2) and further with a dehydratable crosslinking agent (c1), thereby subjecting the water-absorbent resin powder (a) to crosslinking treatment, wherein the water-absorbent resin powder (a) contains an acid group, and wherein the dehydratable crosslinking agent (c1) is reactable with the acid group.

Furthermore, another production process for a water-absorbing agent, according to the present invention, is characterized by comprising the step of blending a water-absorbent resin powder (a1) with a noncrosslinkable water-soluble inorganic base (b1) and/or an irreducible alkaline-metal-salt pH buffer (b2) and further with a crosslinking agent (c), thereby subjecting the water-absorbent resin powder (a1) to crosslinking treatment, wherein the water-absorbent resin powder (a1) contains an acid group and has a weight-average particle diameter of 300 to 600 μm wherein the ratio of fine powders having particle diameters of not larger than 150 μm in the water-absorbent resin powder (a1) is not more than 10 weight %, and wherein the crosslinking agent (c) is reactable with the acid group.

In addition, a sanitary material, according to the present invention, comprises the water-absorbing agent according to the present invention.

These and other objects and the advantages of the present invention will be more fully apparent from the following detailed disclosure.

EXPLANATION OF THE SYMBOLS

Figure 1:
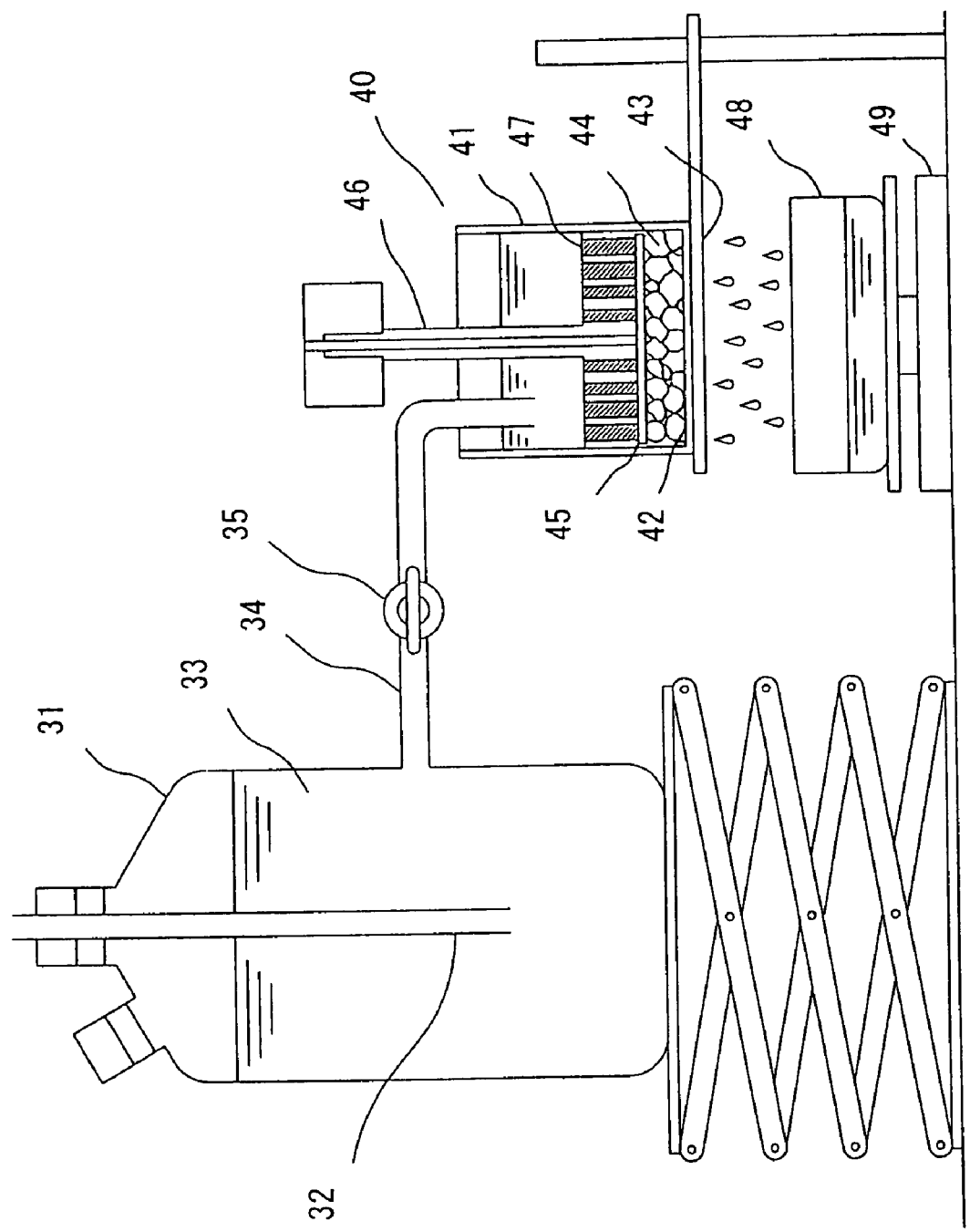
FIG. 1 is a schematic sectional view of a measurement apparatus as used for measuring the saline flow conductivity.

| | |
|---|---|
| 31: | Tank |
| 32: | Glass tube |
| 33: | 0.69 weight % aqueous sodium chloride solution |
| 34: | L-tube having cock |
| 35: | Cock |
| 40: | Receptacle |
| 41: | Cell |
| 42: | Stainless wire mesh |
| 43: | Stainless wire mesh |
| 44: | Swollen gel |
| 45: | Glass filter |

-continued

| | |
|---|---|
| 46: | Piston |
| 47: | Holes in piston |
| 48: | Collecting receptacle |
| 49: | Balance |
| 51: | Glass receptacle |
| 52: | Disperser |
| 53: | Upper clamp |
| 54: | Lower clamp |

DETAILED DESCRIPTION OF THE INVENTION

Hereinafter, the present invention is explained in detail. Incidentally, hereinafter, what is referred to as the water-absorbing agent in the present invention comprises a water-absorbent resin having a crosslinked structure (hereinafter, referred to as a water-absorbent resin simply) as a major component (in a ratio of favorably 50 to 100 weight %, more favorably 80 to 100 weight %, still more favorably 90 to 100 weight %), wherein the water-absorbent resin is a further modified (favorably surface-modified, particularly surface-crosslinked) one with a crosslinking agent.

(Production Process for Water-absorbent Resin):

Hereinafter, in the present invention, a water-absorbent resin powder containing an acid group is referred to as a water-absorbent resin powder (a). Of the water-absorbent resin powders (a), a powder of which the particle diameter is further controlled, for example, a powder having a weight-average particle diameter of 300 to 600 μm wherein the ratio of fine powders having particle diameters of not larger than 150 μm in the water-absorbent resin powder (a) is not more than 10 weight %, is referred to as a water-absorbent resin powder (a1).

The water-absorbent resin of the present invention means a water-absorbent resin that has been known hitherto, for example, a conventionally known crosslinked polymer that absorbs essentially not less than 5 times, favorably 50 to 1,000 times as large a quantity of water as the original weight in deionized water, and thereby forms an anionic, nonionic, or cationic water-insoluble hydrogel.

These are generally particulate water-absorbing agents of which the major proportions are comprised of water-absorbent resins that are obtained by a process including the step of polymerizing unsaturated monomer components (favorably acid-group-containing unsaturated monomers, particularly carboxyl-group-containing unsaturated monomers) and have crosslinked structures, and are obtained by a process including the steps of: polymerizing in a state of an aqueous monomer solution; if necessary, drying this resultant polymer; and usually pulverizing the resultant polymer before and/or after the drying. Examples of such water-absorbent resins include at least one member of the following materials: partially neutralized poly(acrylic acids); hydrolyzed graft polymers of starch-acrylonitrile; graft polymers of starch-acrylic acid; saponified copolymers of vinyl acetate-acrylate esters; hydrolyzed copolymers of acrylonitrile or acrylamide, or crosslinked polymers of these hydrolyzed copolymers; modified polymers of carboxyl-group-containing crosslinked poly(vinyl alcohols); and crosslinked copolymers of isobutylene-maleic anhydride.

These water-absorbent resins can be used either alone respectively or in combinations with each other. Among them, water-absorbent resins containing an acid group, and further one or mixtures of those which have a carboxyl group and are carboxylic acids or their salts are favorable, and it is typical that the water-absorbent resin comprises a polymer as a major component wherein the polymer is a polymer obtained by a process including the steps of: polymerizing monomers including acrylic acid and/or its salt (neutralized product) as a main component; and then crosslinking the resultant polymer, namely, a crosslinked poly(acrylic acid salts), if necessary, containing a graft component.

In addition, it is essential that the above water-absorbent resin is water-swellable and water-insoluble, and the uncrosslinked water-extractable content (water-soluble polymer) in the water-absorbent resin as used is favorably not more than 50 weight %, more favorably not more than 25 weight %, still more favorably not more than 20 weight %, yet still more favorably not more than 15 weight %, particularly favorably not more than 10 weight %.

Examples of the above acrylic acid salts include: acrylic acid salts of alkaline metals, such as sodium, potassium, and lithium; ammonium salts and amine salts of acrylic acid. The constituent units of the above water-absorbent resin comprise: acrylic acid of favorably 0 to 50 mol %, more favorably 10 to 40 mol %; and an acrylic acid salt of favorably 100 to 50 mol %, more favorably 90 to 60 mol % (wherein the total of both is not more than 100 mol %). Incidentally, the molar ratio between this acid and its salt is referred to as a neutralization ratio. The neutralization of the water-absorbent resin so as to form the above salt may be carried out in a state of a monomer before the polymerization, or in a state of a polymer during or after the polymerization, or in combinations with each other.

In general, in the case where an unneutralized or low neutralized monomer is polymerized and where the neutralization is then carried out in a state of a polymer (acid-type polymerization method), it tends to obtain a water-absorbent resin having a high absorption capacity and a low extractable content, but it takes considerably lots of labor, facilities, and time to uniformly neutralize individual particles of the water-absorbent resin (JP-A-010173/1998). However, if the present invention process is employed, all water-absorbent resins can favorably be used for such as surface-crosslinking regardless of the neutralized state of the water-absorbent resins and their production processes. Thereby, the properties and productivity of the water-absorbing agent can greatly be improved.

The monomer to obtain the water-absorbent resin as used in the present invention may further comprise monomers other than the above acrylic acid (salt) when the occasion demands. There is no especial limitation on the monomers other than the acrylic acid (salt), but specific examples of the above other monomers include: anionic unsaturated monomers, such as methacrylic acid, maleic acid, vinylsulfonic acid, styrenesulfonic acid, 2-(meth)acrylamido-2-methylpropanesulfonic acid, 2-(meth)acryloylethanesulfonic acid, and 2-(meth)acryloylpropanesulfonic acid, and salts thereof, nonionic hydrophilic-group-containing unsaturated monomers, such as acrylamide, methacrylamide, N-ethyl(meth)acrylamide, N-n-propyl(meth)acrylamide, N-isopropyl (meth)acrylamide, N,N-dimethyl(meth)acrylamide, 2-hydroxyethyl (meth)acrylate, 2-hydroxypropyl (meth)acrylate, methoxypolyethylene glycol (meth)acrylate, polyethylene glycol mono(meth)acrylate, vinylpyridine, N-vinylpyrrolidone, N-acryloylpiperidine, and N-acryloylpyrrolidine; and cationic unsaturated monomers, such as N,N-dimethylaminoethyl (meth)acrylate, N,N-diethylaminoethyl (meth)acryl ate, N,N-dimethylaminopropyl (meth)acryl ate, and N,N-dimethylaminopropyl(meth)acrylamide, and quaternary salts thereof. These monomers may be used either alone respectively or in combinations with each other.

In the present invention, when the monomers other than the acrylic acid (salt) are used, the ratio of these monomers other than the acrylic acid (salt) is favorably not more than 30 mol %, more favorably not more than 10 mol %, relative to the total of the acrylic acid and its salt used as the major components. If the above monomers other than the acrylic acid (salt) are used in the above ratio, then the absorption properties of the water-absorbent resin (water-absorbing agent) as finally obtained are still more improved, and further, the water-absorbent resin (water-absorbing agent) can be obtained at still lower costs.

When the above-mentioned monomers are polymerized in order to obtain the water-absorbent resin as used in the present invention, bulk polymerization or precipitation polymerization can be carried out. However, from the viewpoint of the performance or the easiness of controlling the polymerization and further the absorption properties of swollen gels, aqueous solution polymerization or reversed-phase suspension polymerization is favorably carried out using the above monomers in the form of their aqueous solution. Incidentally, when the above monomers are used in the form of their aqueous solution, their concentration in the aqueous solution (hereinafter referred to as aqueous monomer solution) depends upon the temperature of the aqueous solution or upon the monomers. Although there is no especial limitation, the concentration is favorably in the range of 10 to 70 weight %, more favorably 20 to 60 weight %. In addition, when the above aqueous solution polymerization is carried out, solvents other than water may be jointly used when the occasion demands, and there is no limitation on the kinds of the solvents as jointly used.

Examples of the method of the aqueous solution polymerization include: a method that involves polymerizing the aqueous monomer solution in a double-arm type kneader while the resultant hydrogel is pulverized; and a method that involves supplying the aqueous monomer solution into a predetermined vessel or onto a moving belt and pulverizing the resultant gel from the polymerization with such as a meat chopper.

When the above polymerization is initiated, the following polymerization initiators, for example, can be used: radical polymerization initiators, such as potassium persulfate, ammonium persulfate, sodium persulfate, t-butyl hydroperoxide, hydrogen peroxide, and 2,2'-azobis(2-amidinopropane) dihydrochloride; and photopolymerization initiators such as 2-hydroxy-2-methyl-1-phenyl-propan-1-one.

Furthermore, redox initiators are also available by further using a reductant to promote decomposition of the above polymerization initiator and combining both. Examples of the above reductant include: (bi)sulfurous acid (or its salts) such as sodium sulfite and sodium hydrogensulfite; L-ascorbic acid (or its salts); reducible metals (or their salts) such as ferrous salts; and amines. However, there is no especial limitation on the reductants.

The amount of these polymerization initiators as used is in the range of usually 0.001 to 2 mol %, favorably 0.01 to 0.1 mol %. In the case where the amount of these polymerization initiators is smaller than 0.001 mol %, there are disadvantages in that the amount of unreacted monomers is increased, and therefore the residual amount of the monomers is increased in the resultant water-absorbent resin or water-absorbing agent. On the other hand, in the case where the amount of these polymerization initiators is larger than 2 mol %, there may be disadvantages in that the water-extractable content in the resultant water-absorbent resin or water-absorbing agent is increased.

In addition, the polymerization reaction may be initiated by irradiating the reaction system with active energy rays, such as radiations, electron beams, and ultraviolet rays, or further using the above polymerization initiators jointly therewith. Incidentally, the reaction temperature is not especially limited in the above polymerization reaction, but it is favorably in the range of 15 to 130° C., more favorably 20 to 120° C. In addition, there is no especial limitation on the reaction time and polymerization pressure either, and they may fitly be determined according to factors such as the respective kinds of the monomers and polymerization initiators and the reaction temperature.

The aforementioned water-absorbent resin may be a self-crosslinking-type water-absorbent resin obtained by using no crosslinking agent, but it is favorably obtained by copolymerizing or reacting with a crosslinking agent (internal-crosslinking agent for water-absorbent resins) having at least two polymerizable unsaturated groups or at least two reactive groups per molecule.

Specific examples of these internal-crosslinking agents include: N,N'-methylenebis(meth)acryl amide, (poly)ethylene glycol di(meth)acrylate, (poly)propylene glycol di(meth)acrylate, trimethylolpropane tri(meth)acrylate, glycerol tri(meth)acrylate, glycerol acrylate methacrylate, ethylene-oxide-modified trimethylolpropane tri(meth)acrylate, pentaerythritol hexa(meth)acrylate, triallyl cyanurate, triallyl isocyanurate, triallyl phosphate, triallylamine, poly (meth)allyloxyalkanes, (poly)ethylene glycol diglycidyl ether, glycerol diglycidyl ether, ethylene glycol, polyethylene glycol, propylene glycol, glycerol, pentaerythritol, ethylenediamine, ethylene carbonate, propylene carbonate, polyethylenimine, and glycidyl (meth)acrylate.

These internal-crosslinking agents may be used either alone respectively or in combinations with each other. In addition, these internal-crosslinking agents may be added to the reaction system either all at once or divisionally. When at least one or at least two kinds of internal-crosslinking agents are used, it is favorable to essentially use a compound having at least two polymerizable unsaturated groups in the polymerization step in consideration of such as absorption properties of the finally obtained water-absorbent resin or water-absorbing agent.

The amount of these internal-crosslinking agents as used is in the range of favorably 0.001 to 2 mol %, more favorably 0.005 to 0.5 mol %, still more favorably 0.01 to 0.2 mol %, particularly favorably 0.03 to 0.15 mol %, of the aforementioned monomers (excluding the crosslinking agent). In the case where the amount of the above internal-crosslinking agent as used is smaller than 0.001 mol % or larger than 2 mol %, the absorption properties might not be obtained sufficiently.

When the crosslinked structure is introduced into the internal portion of the polymer by using the above internal-crosslinking agent, the above internal-crosslinking agent may be added to the reaction system before, during or after polymerization of the above monomers, or after neutralization.

Incidentally, when the above polymerization is carried out, 0 to 50 weight % (relative to the monomers) of hydrophilic polymers (e.g. starch, cellulose, derivatives from starch, derivatives from cellulose; polyvinyl alcohol, polyacrylic acid (salts), and crosslinked products of polyacrylic acid (salts)) and 0 to 10 weight % of other components (e.g. various foaming agents, such as (hydrogen) carbonates, carbon dioxide, azo compounds, and inert organic solvents; various surfactants; chelating agents; and chain transfer agents such as hypophosphorous acid (salts)) may be added to the reaction system.

When the above crosslinked polymer is a gel as obtained by the aqueous solution polymerization, namely, a crosslinked hydrogel polymer, the crosslinked polymer is dried, if necessary, and usually pulverized before or after drying in order to produce a water-absorbent resin. In addition, the drying is carried out at a temperature of usually 60 to 250° C., favorably 100 to 220° C., more favorably 120 to 200° C. The drying time depends upon the surface area and water content of the polymer, and the kinds of dryers, and is selected in such a way as to give the aimed water content.

The water content (as defined by a water content included in the water-absorbent resin or the water-absorbing agent and measured by the weight loss on drying at 180° C. for 3 hours) of the water-absorbent resin or the water-absorbing agent usable in the present invention is not especially limited. However, the water-absorbent resin is a powder exhibiting fluidity even at room temperature from the viewpoint of properties of the resultant water-absorbing agent, and it is in a powdery state where the water content is more favorably in the range of 0.2 to 30 weight %, still more favorably 0.3 to 15 weight %, particularly favorably 0.5 to 10 weight %.

In addition, examples of the water-absorbent resin usable for the production process according to the present invention include powdery ones. As to particles of the water-absorbent resin, those which have an average particle diameter of larger than 1,000 μm in the form of an undried and unpulverized gel obtained by the polymerization reaction can also be used. However, such particles are usually not formed into a powder, therefore, if necessary (favorably), they are adjusted by the drying, pulverization, and classification so as to have a powder particle diameter to meet the purpose.

As to the particle diameter of the water-absorbent resin powder or the water-absorbing agent, the weight-average particle diameter is used in the range of 10 to 2,000 μm, favorably 100 to 1,000 μm, more favorably 200 to 700 μm, still more favorably 300 to 600 μm, particularly favorably 400 to 550 μm. Further favorably, the water-absorbent resin powder or the water-absorbing agent favorably contains fine powder (e.g. not larger than 100 μm, favorably not larger than 150 μm) in as small an amount as possible, specifically, in a ratio of not more than 10 weight %, more favorably not more than 5 weight %, particularly favorably not more than 1 weight %. In addition, in the water-absorbent resin powder or the water-absorbing agent, the ratio of particles having particle diameters of favorably substantially not smaller than 1,000 μm, more favorably not smaller than 850 μm, is favorably not more than 5 weight %, more favorably not more than 1 weight %.

The particle shape of the water-absorbent resin or the water-absorbing agent as obtained in this way is such as spherical, pulverized, or irregular shape and not especially limited. However, a water-absorbent resin having irregular pulverized shape as obtained through a pulverization step can favorably be used. Furthermore, the bulk density (defined by JIS K-3362) is favorably in the range of 0.40 to 0.80 g/ml, more favorably 0.50 to 0.75 g/ml, still more favorably 0.60 to 0.73 g/ml, from the viewpoint of excellent properties of the water-absorbing agent.

The water-absorbent resin as obtained in the above method usually displays a saturated absorption capacity of about 10 to about 100 g/g without load for a physiological saline, and the properties such as this absorption capacity can fitly be adjusted according to the purpose.

(Water-soluble Inorganic Base (b1)):

In the present invention, the noncrosslinkable water-soluble inorganic base (b1) (namely, the water-soluble inorganic base (b1) favorably selected from the group consisting of: alkaline metal salts, ammonium salts, alkaline metal hydroxides, and ammonia or its hydroxide) (hereinafter, referred to as water-soluble inorganic base (b1)) and/or the irreducible alkaline-metal-salt pH buffer (b2), and further the crosslinking agent (c) or dehydratable crosslinking agent (c1) are added to the above water-absorbent resin powder (a) or (a1). Hereinafter, the water-soluble inorganic base (b1) is explained.

That is to say, in the present invention, the water-soluble inorganic base means an inorganic compound (including carbonates and bicarbonates) that: dissociates in an aqueous solution and thereby forms OH$^-$ from water or this base; and forms a salt by neutralizing an acid group. The water-soluble inorganic base (b1) as used in the present invention is favorably selected from the group consisting of: alkaline metal salts, ammonium salts, alkaline metal hydroxides, and ammonia or its hydroxide, and these are usually substantially noncrosslinkable water-soluble inorganic bases (incidentally, hydroxides of multivalent metals as represented by calcium hydroxide and aluminum hydroxide may be exemplified as examples of crosslinkable water-soluble inorganic bases for the acid-group-containing water-absorbent resin, but, in general, these multivalent metals are not included in the water-soluble inorganic base of the present invention).

It is essential that the water-soluble inorganic base (b1) is water-soluble from the viewpoint of the properties of the water-absorbing agent as obtained, and the base usually having a solubility of not less than 5 g (favorably not less than 20 g, more favorably not less than 50 g, still more favorably not less than 100 g) per 100 g of water at room temperature is used. Incidentally, in the present invention, it is not excluded that such as non-water-soluble inorganic bases, organic bases, and crosslinkable inorganic bases (hydroxides of multivalent metals) are jointly used. However, when the noncrosslinkable water-soluble inorganic base (b1) is not used, the properties of the water-absorbing agent as obtained are low.

Specific examples of the water-soluble inorganic base (b1) include: carbonic compounds including alkaline metal salts and/or ammonium salts, such as lithium carbonate, sodium carbonate, potassium carbonate, sodium potassium carbonate, cesium carbonate, rubidium carbonate, and ammonium carbonate; their hydrates (e.g. decahydrates, heptahydrates, 1.5 hydrates, and monohydrates); bicarbonates including alkaline metal salts and/or ammonium salts, such as lithium bicarbonate, sodium bicarbonate, potassium bicarbonate, cesium bicarbonate, rubidium bicarbonate, and ammonium bicarbonate; hydroxide compounds including alkaline metal salts and ammonium salts, such as lithium hydroxide, sodium hydroxide, potassium hydroxide, cesium hydroxide, rubidium hydroxide, ammonium hydroxide and water glass; hydrogenphosphate compounds, such as disodium hydrogenphosphate, dipotassium hydrogenphosphate, dilithium hydrogenphosphate, dirubidium hydrogenphosphate, and dicesium hydrogenphosphate; double salts, such as sodium sesquicarbonate ($Na_2CO_3 \cdot NaHCO_3 \cdot 2H_2O$). At least two kinds of these may be blended or used together. In addition, these water-soluble inorganic bases (b1) are purchased, preserved, and used as powders, their hydrates, pellets, or aqueous solutions, but there is no especial limitation on their forms.

Of the water-soluble inorganic bases (b1), what are favorably used from the viewpoint of the properties and solubility are the alkaline metal salts, more favorably the lithium salts, sodium salts, or potassium salts, still more favorably the sodium salts. In addition, of the compounds (b1), what are favorably used from the viewpoint of the properties are the carbonates/hydrogencarbonates/hydroxides, more favorably the hydroxides and/or hydrogencarbonates, particularly favorably the hydroxides. That is to say, specifically, what are favorably used as the water-soluble inorganic base (b1) are sodium hydrogencarbonate and/or sodium hydroxide, more favorably the sodium hydroxide.

When the water-soluble inorganic base (b1) is not used together with the below-mentioned irreducible alkaline-metal-salt pH buffer (b2), the amount of the water-soluble inorganic base (b1) as used in the present invention is favorably in the range of 0.001 to 10 parts by weight, more favorably 0.01 to 5 parts by weight, still more favorably 0.01 to 2 parts by weight, per 100 parts by weight of the water-absorbent resin. If the water-soluble inorganic base (b1) is used in the above range, the absorption properties for body fluids (aqueous liquids) such as urine, sweat, and menstrual blood can be improved further more. In the case where the amount as used is smaller than 0.001 part by weight, the neutralization ratio of the functional group in the surface neighborhood of the water-absorbent resin cannot be moderately controlled, and the absorption properties may not be improved. In the case where the amount as used is larger than 10 parts by weight, it is in excess and uneconomical, and further there is a possibility that the absorption capacity is not improved.

Incidentally, when the water-soluble inorganic base (b1) is used together with the below-mentioned irreducible alkaline-metal-salt pH buffer (b2), the total amount of them as used is favorably in the range of 0.001 to 10 parts by weight, more favorably 0.01 to 5 parts by weight, still more favorably 0.01 to 2 parts by weight, per 100 parts by weight of the water-absorbent resin by the same reason as mentioned above. However, when the water-soluble inorganic base (b1) is used together with the below-mentioned irreducible alkaline-metal-salt pH buffer (b2) in the present invention, the water-soluble inorganic base (b1) and the irreducible alkaline-metal-salt pH buffer (b2) are jointly used fitly in such a range as to exhibit action of at least either one of them.

This mechanism of improving the absorption properties is not apparent, but the following two reasons are presumed: (1) the formation of uniformly surface-crosslinked layers by rendering the surface neutralization ratio uniform, and (2) the optimization of blending and absorptivity by changing the salt concentration.

That is to say, as to the reason (1), generally in the case of the water-absorbent resin powder, whether the post-neutralization is carried out after polymerization or not (whether the aforementioned neutralization polymerization method or acid-type polymerization method is carried out), the neutralization ratios of individual particles of the water-absorbent resin powder are different and, even as to an identical particle of the powder, the neutralization ratio microscopically differs throughout the surface of this particle. Therefore, in the conventional surface treatment, the non-uniformity of the crosslinking reaction of the powder or the blending of the crosslinking agent has been caused by these reasons, and the decrease of properties has been arisen. Thus, because the difference between the neutralization ratios of individual particles of the water-absorbent resin powder and the microscopic difference in the neutralization ratio throughout the surface of one particle of the powder are removed by jointly using the water-soluble inorganic base (b1) and the crosslinking agent (c) in the present invention, the neutralization of the carboxyl groups concerning the crosslinking and existing in the surface neighborhood can uniformly be optimized. As a result, it has become possible that the surface-crosslinking is uniformly carried out. For example, the neutralization ratio of a water-absorbing agent as obtained from a poly(acrylic acid) water-absorbent resin having a neutralization ratio of 70 mol % and 0.01 to 2 parts by weight of sodium hydroxide is raised to the range of 0.025 to 5 mol %, and further the neutralization ratio in the surface neighborhood of the particle is selectively high. Furthermore, it is presumed that the water-soluble inorganic base (b1) of the present invention acts also as a reaction catalyst of the crosslinking agent, and that this action causes the improvement of the absorption properties.

In addition, as to the reason (2), when the crosslinking agent is blended, the water-soluble inorganic base (b1) controls the absorptivity to the water-absorbent resin due to the high salt concentration in the crosslinking agent solution, and thereby improves the blendability. However, the water-soluble inorganic base (b1) disappears from the crosslinking agent solution by, after the blending, carrying out a neutralization reaction with a carboxyl group of the water-absorbent resin to form its alkaline metal salt or ammonium salt. Therefore, it is presumed that the water-soluble inorganic base (b1) acts to promote the absorptivity of the crosslinking agent. This is presumed that: conventional additives (e.g. hydrophilic organic solvent such as isopropanol) control the absorptivity to the water-absorbent resin due to the inert organic solvent, and thereby improve the blendability, but the absorptivity of the crosslinking agent into the surface is unfavorably inhibited because the organic solvent remains in the crosslinking agent solution still after the blending.

In addition, unlike the case of the water-soluble inorganic base (b1), when a salt of a multivalent metal (e.g. aluminum) is used, it is presumed that the crosslinking reaction proceeds unfavorably by a multivalent metal ion, so that the absorption capacity without load or under a load is caused to decrease. Furthermore, it is also presumed that the crosslinking caused by the multivalent metal ion is very weak because of forming an ionic bond, and that the decrease of the properties are caused further more because the multivalent metal ion moves into the particle in a water-swollen state and thereby forms the crosslinking.

It is presumed that the water-soluble inorganic base (b1) of the present invention improves conventional demerits such that: the thickness of a crosslinked layer of the water-absorbing agent is short, and the properties are decreased, wherein the demerits are caused by the aforementioned phenomena. It is also presumed that if a dehydratable crosslinking agent (c1) is further used, then the crosslinking agent further absorbs into the surface neighborhood by water as generated from a dehydration crosslinking reaction, and the thickness of the crosslinked layer is more increased.

(Irreducible Alkaline-metal-salt pH Buffer (b2)):

In the present invention, the noncrosslinkable water-soluble inorganic base (b1) (namely, the water-soluble inorganic base (b1) selected from the group consisting of: alkaline metal salts, ammonium salts, alkaline metal hydroxides, and ammonia or its hydroxide) and/or the irreducible alkaline-metal-salt pH buffer (b2), and further the crosslinking agent (c) or dehydratable crosslinking agent. (c1) are added to the above water-absorbent resin powder (a) or (a1). Hereinafter, the irreducible alkaline-metal-salt pH buffer (b2) is explained.

The irreducible alkaline-metal-salt pH buffer (b2) in the present invention maintains almost a constant concentration of hydrogen ion even if an acid or base is added or disappears to some extent in a solution, and this buffer (b2) is essentially irreducible, and favorably a further non-oxidizable alkaline-metal salt is used therefor (e.g. in the case of an irreducible alkaline-metal-salt pH buffer containing such as phosphorus or sulfur, if the oxidation number of the phosphorus atom is +5 or the oxidation number of the sulfur atom is +6, this pH buffer displays non-oxidizability and irreducibility.).

When the pH buffer has reducibility or is not an alkaline metal salt, there is a possibility of inhibiting the crosslinking, and the object of the present invention cannot be achieved sufficiently. In the present invention, the alkaline metal salt acts as the pH buffer, and pH buffers as prepared from combinations of various acids, bases, or salts are applied thereto. In addition, the molecular weight of the pH buffer as used is favorably in the range of 50 to 1,000, more favorably 60 to 800, particularly favorably 70 to 500, from the viewpoint of blendability and absorptivity to the water-absorbent resin.

Representative examples of the alkaline metal salt acting as the pH buffer (b2) as referred to in the present invention include at least one member selected from the group consisting of hydrogencarbonates, dihydrogenphosphates, and hydrogenphosphates.

Specific examples thereof include: partial alkaline-metal salts of inorganic polybasic acids, such as sodium hydrogencarbonate, potassium hydrogencarbonate, lithium hydrogencarbonate, sodium dihydrogenphosphate, potassium dihydrogenphosphate, disodium hydrogenphosphate, and dipotassium hydrogenphosphate; and partial alkaline-metal salts (particularly, sodium or potassium salts, and further, lithium salts) of organic polycarboxylic acids, such as potassium dihydrogencitrate, sodium dihydrogencitrate, disodium hydrogencitrate, dipotassium hydrogencitrate, sodium hydrogentartrate, potassium hydrogentartrate, monosodium fumarate, and potassium hydrogenphthalate.

In addition, representative examples of the pH buffers (b2) as prepared from combinations of various acids, bases, or salts in the present invention, besides the above pH buffer (b2), include a buffer as prepared from combinations of compounds that are used for preparing conventionally known buffer solutions. The buffer solution is a solution of the buffer, particularly an aqueous solution of: a salt comprising a combination of a weak acid and a strong base; or a salt comprising a combination of a strong acid and a weak base; or a mixture of these salts. In the case of the water-absorbent resin containing an acid group such as a carboxyl group, a buffer as a salt mixture comprised of a weak acid and a strong base is favorably used, and an inorganic salt is more favorably used.

As to the buffer solutions, specific examples thereof include combination of compounds as used for buffer solutions as described in *The Chemical Handbook* (edited by the Chemical Society of Japan, 11-355, 356). Examples thereof include: a Clark-Lubs buffer solution (potassium chloride/hydrochloric acid; pH 1.0 to 2.2, potassium hydrogenphthalate/hydrochloric acid; pH 2.2 to 3.8, potassium hydrogenphthalate/sodium hydroxide; pH 4.0 to 6.2, potassium dihydrogenphosphate/sodium hydroxide; pH 5.8 to 8.0, and boric acid/potassium chloride/sodium hydroxide; pH 7.8 to 10.0); a SΦrensen buffer solution (glycine+sodium chloride/hydrochloric acid; pH 1.1 to 4.6, glycine+sodium chloride/hydrochloric acid; pH 8.6 to 13.0, sodium citrate/hydrochloric acid; pH 1.1 to 4.9, sodium citrate/sodium hydroxide; pH 5.0 to 6.7, sodium tetraborate/hydrochloric acid; pH 7.6 to 9.2, sodium tetraborate/sodium hydroxide; pH 9.3 to 12.4, and potassium dihydrogenphosphate/disodium hydrogenphosphate; pH 5.3 to 8.0); a Kolthoff buffer solution (potassium citrate/citric acid; pH 2.2 to 3.6, potassium dihydrogencitrate/hydrochloric acid; pH 2.2 to 3.6, potassium dihydrogencitrate/sodium hydroxide; pH 3.8 to 6.0, succinic acid/sodium tetraborate; pH 3.0 to 5.8, potassium dihydrogencitrate/sodium tetraborate; pH 3.8 to 6.0, potassium dihydrogenphosphate/sodium tetraborate; pH 5.8 to 9.2, sodium tetraborate/sodium carbonate; pH 9.2 to 11.0, hydrochloric acid/sodium carbonate; pH 10.2 to 11.2, and disodium hydrogenphosphate/sodium hydroxide; pH 11.0 to 12.0); a Michaelis buffer solution (tartaric acid/sodium tartrate; pH 1.4 to 4.5, lactic acid/sodium lactate; pH 2.3 to 5.3, acetic acid/sodium acetate; pH 3.2 to 6.2, potassium dihydrogenphosphate/disodium hydrogenphosphate; pH 5.2 to 8.3, sodium diethylbarbiturate+sodium acetate/hydrochloric acid; pH 2.6 to 9.2, sodium diethylbarbiturate/hydrochloric acid; pH 6.8 to 9.6, and N,N-dimethylglycine sodium salt/hydrochloric acid; pH 8.6 to 10.6); a Mcilvaine wide-ranging buffer solution (disodium hydrogenphosphate/citric acid; pH 2.2 to 8.0); a Britton-Robinson wide-ranging buffer solution (citric acid+potassium dihydrogenphosphate+boric acid+diethylbarbituric acid/trisodium phosphate); a Carmody wide-ranging buffer solution (boric acid+citric acid/trisodium phosphate; pH 2.0 to 12.0), a Gomori buffer solution (2,4,6-trimethylpyridine/hydrochloric acid; pH 6.4 to 8.4, tris(hydroxymethyl)aminomethane/hydrochloric acid; pH 7.2 to 9.1, 2-amino-2-methyl-1,3-propanediol/hydrochloric acid; pH 7.8 to 9.7); a Tris buffer solution of Bates-Bower (tris(hydroxymethyl)aminomethane/hydrochloric acid; pH 7.0 to 9.0); and a Delory-King buffer solution (carbonate salts/hydrogencarbonate salts; pH 9.2 to 10.7). Then, the pH and concentration of the buffer as used are dependent upon the neutralization ratio of the water-absorbent resin or the kind of the surface-crosslinking agent as used, but the pH of the surface-crosslinking agent solution is favorably adjusted to the range of 1.5 to 10.0 by adding the buffer.

Of the above, a partially neutralized salt of an inorganic polybasic acid is favorable, and a partially alkaline-metal-neutralized salt of phosphoric acid or carbonic acid is more favorable, from the viewpoint of such as properties, stability, use in one-component system, and costs.

When the pH buffer (b2) is not used together with the above water-soluble inorganic base (b1), the amount of the above pH buffer (b2) as used in the present invention is favorably in the range of 0.005 to 10 parts by weight, more favorably 0.05 to 5 parts by weight, per 100 parts by weight of the water-absorbent resin in terms of solid content. If the pH buffer (b2) is used in the above range, the absorption properties for body fluids (aqueous liquids) such as urine, sweat, and menstrual blood can be improved further more. In the case where the amount as used is smaller than 0.005 part by weight, the neutralization ratio of the functional group in the surface neighborhood of the water-absorbent resin cannot be moderately controlled, and the absorption properties may not be improved. In the case where the amount of the pH buffer (b2) as used is larger than 10 parts by weight, the additive is in excess and uneconomical, and further there is a possibility that the absorption capacity is not improved.

Incidentally, when the irreducible alkaline-metal-salt pH buffer (b2) is used together with the aforementioned water-soluble inorganic base (b1), the total amount of them as used is favorably in the range of 0.001 to 10 parts by weight, more favorably 0.01 to 5 parts by weight, still more favorably 0.01 to 2 parts by weight, per 100 parts by weight of the water-absorbent resin by the same reason as mentioned above. However, when the water-soluble inorganic base (b1) is used together with the aforementioned irreducible alkaline-metal-salt pH buffer (b2) in the present invention, the water-soluble inorganic base (b1) and the irreducible alkaline-metal-salt pH buffer (b2) are jointly used fitly in such a range as to exhibit action of at least either one of them.

The mechanism of improving these absorption properties is not apparent, but the following both two reasons are presumed: (1) rendering the surface neutralization ratio uniform, and (2) the optimization of blending and absorptivity by changing the salt concentration.

That is to say, as to the reason (1), in the case of the water-absorbent resin powder, whether the post-neutralization is carried out after polymerization or not (whether the aforementioned neutralization polymerization method or acid-type polymerization method is carried out), the neutralization ratios of individual particles of the water-absorbent resin powder are different and, even as to an identical particle of the powder, the neutralization ratio microscopically differs throughout the surface of this particle. Therefore, the non-uniformity of the crosslinking reaction of the powder or the blending of the crosslinking agent has been caused, and the decrease of properties has been arisen. However, because the difference between the neutralization ratios of individual particles of the water-absorbent resin powder and the microscopic difference in the neutralization ratio throughout the surface of one particle of the powder are removed by jointly using the pH buffer (b2) of the present invention together with the crosslinking agent (b), it is thought because the neutralization of the carboxyl groups concerning the crosslinking and existing in the surface neighborhood can uniformly be optimized in the present invention, regardless of the neutralization ratio and the below-mentioned neutralization index of the water-absorbent resin powder. As a result, it is presumed that: the pH buffer of the present invention acts also as a blending promoter without inhibiting the absorptivity of the crosslinking agent to the water-absorbent resin powder and further acts also as a reaction catalyst of the crosslinking agent, and these actions cause the improvement of the absorption properties.

In addition, as to the reason (2), the pH buffer such as a hydrogencarbonate salt exists as its alkaline metal salt in a crosslinking agent solution when the crosslinking agent is blended. Therefore, the pH buffer controls the absorptivity to the water-absorbent resin due to the high salt concentration, and thereby improves the blendability. However, the alkaline metal salt of the pH buffer disappears from the crosslinking agent solution by, after the blending, carrying out a neutralization reaction with a carboxyl group of the water-absorbent resin. Therefore, it is presumed that the salt inhibiting the absorptivity of the crosslinking agent disappears after the blending, and thereby the pH buffer acts to promote the absorptivity of the crosslinking agent. This is presumed that: conventional additives (e.g. hydrophilic organic solvent such as isopropanol) control the absorptivity to the water-absorbent resin due to the inert organic solvent, and thereby improve the blendability, but the absorptivity of the crosslinking agent into the surface is unfavorably inhibited because the organic solvent remains in the crosslinking agent solution still after the blending, and thereby the pH buffer of the present invention improves conventional demerits of shorting the thickness of the crosslinked layer of the water-absorbing agent.

(Crosslinking Agent (c) and its Blending and Crosslinking Treatment):

In the present invention, it is favorable to use a surface-crosslinking agent, more favorably the dehydratable (dehydration-reactable) crosslinking agent (c1), as the crosslinking agent (c) reactable with an acid group. Incidentally, the term "dehydratable (dehydration-reactable)" means a crosslinking agent that causes crosslinking by a dehydration reaction between the functional group of the water-absorbent resin (especially, the functional group in the surface neighborhood) and the crosslinking agent, favorably by a dehydration esterification and/or dehydration amidation, more favorably by a dehydration esterification.

Specifically, when the water-absorbent resin contains a carboxyl group, examples of the crosslinking agent (c1) that exhibits dehydratability include: hydroxyl-group-containing crosslinking agents such as polyhydric alcohols; amino-group-containing crosslinking agents such as polyamines; and further, cyclic crosslinking agents, such as alkylene carbonates, mono-, di-, or polyoxazolidinone compounds, and oxetane compounds (e.g. 3-methyl-3-oxetane methanol) wherein hydroxyl groups or amino groups are formed in the accompaniment with a ring-opening reaction of the cyclic crosslinking agents and carry out a crosslinking reaction. The dehydratable crosslinking agents (c1) can be used either alone respectively or in combinations with each other. However, non-dehydratable crosslinking agents (e.g. multivalent metals) may also be used together further.

Specifically, if the dehydratable crosslinking agent (c1) usable in the present invention is a crosslinking agent reactable with the functional group of the water-absorbent resin, it is used without limitation and is usually a crosslinking agent (surface-crosslinking agent) used for this usage. Examples thereof include: at least one member selected from the group consisting of: polyhydric alcohol compounds, such as ethylene glycol, diethylene glycol, propylene glycol, triethylene glycol, tetraethylene glycol, polyethylene glycol, dipropylene glycol, polypropylene glycol, 1,3-propanediol, 2,2,4-trimethyl-1,3-pentanediol, glycerol, diglycerol, polyglycerol, 2-butene-1,4-diol, 1,4-butanediol, 1,5-pentanediol, 1,6-hexanediol, 1,2-cyclohexanedimethanol, 1,2-cyclohexanol, trimethylolpropane, diethanolamine, triethanolamine, polyoxypropylene, oxyethylene-oxypropylene block copolymers, pentaerythritol, and sorbitol; polyamine compounds, such as ethylenediamine, triethylenetetramine, tetraethylenepentamine, pentaethylenehexamine, polyamidepolyamine, polyallylamine, and polyethylenimine; and condensation products between the polyamine compounds and haloepoxy compounds; alkylene carbonate compounds, such as 1,3-dioxolan-2-one, 4-methyl-1,3-dioxolan-2-one, 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxan-2-one, 4-methyl-1,3-dioxan-2-one, 4,6-dimethyl-1,3-dioxan-2-one, and 1,3-dioxopan-2-one; and polyalkylene carbonate compounds, such ethylene glycol bis(4-methylene-1,3-dioxolan-2-one) ether; mono-, di-, or polyoxazolidinone compounds; oxetane compounds, such a 3-methyl-3-oxetane methanol; and polyoxetane compounds.

Of these dehydratable crosslinking agents, at least one member selected from the group consisting of the polyhydric alcohols, alkylene carbonate compounds, oxazolidinone compounds, and (poly)oxetane compounds are favorable, and at least the polyhydric alcohols are particularly favorably used.

In addition to these dehydratable crosslinking agents (c1), examples of the crosslinking agent (c) further include: epoxy compounds such as ethylene glycol diglycidyl ether, polyethylene glycol diglycidyl ether, glycerol polyglycidyl ether, diglycerol polyglycidyl ether, polyglycerol polyglycidyl ether, polyethylene diglycidyl ether, propylene glycol diglycidyl ether, polypropylene glycol diglycidyl ether, glycidol, and γ-glycidoxypropyltrimethoxysilane; polyisocyanate compounds, such as 2,4-tolylene diisocyanate, and hexamethylene diisocyanate; polyoxazoline compounds, such as 1,2-ethylenebisoxazoline; silane coupling agents, such as γ-glycidoxypropyltrimethoxysilane, and γ-aminopropyltrimethoxysilane; polyaziridine compounds, such as 2,2-bishydroxymethylbutanol-tris[3-(1-aziridinyl)propionate]; and polyvalent metals, such as beryllium, magnesium, calcium, strontium, zinc, aluminum, iron, chromium, manganese, titanium, and zirconium.

Incidentally, the properties of the water-absorbing agent as generally obtained are low when there is used in the present invention neither the dehydratable crosslinking agent (c1), nor the water-absorbent resin powder (a1) and/or a water-absorbent resin powder, wherein the water-absorbent resin powder (a1) has a weight-average particle diameter of 300 to 600 μm wherein the ratio of fine powders having particle diameters of not larger than 150 μm in the water-absorbent resin powder (a1) is not more than 10 weight %, and wherein the water-absorbent resin powder includes particles having particle diameters of smaller than 850 μm but not smaller than 150 μm in a ratio of not less than 90 weight % of all particles of the water-absorbent resin powder, and includes at least two members selected from the group consisting of: particles (A1) having particle diameters of smaller than 850 μm but not smaller than 600 μm; particles (A2) having particle diameters of smaller than 600 μm but not smaller than 500 μm; particles (A3) having particle diameters of smaller than 500 μm but not smaller than 300 μm; and particles (A4) having particle diameters of smaller than 300 μm but not smaller than 150 μm. Therefore, both the dehydratable crosslinking agent (c1) and the water-absorbent resin powder (a1) having the above specific particle diameter distribution are favorably used in the present invention.

When the water-absorbent resin powder (a) or (a1) is blended with the water-soluble inorganic base (b1) and/or the irreducible alkaline-metal-salt pH buffer (b2) and further with the crosslinking agent (c) or (c1) in the present invention, it is favorable to use water. In this case, the amount of water as used depends upon the water content of the water-absorbent resin as used, but it is usually in the range of 0.5 to 20 parts by weight, favorably 0.5 to 10 parts by weight, per 100 parts by weight of the water-absorbent resin. In the case where the amount of water as used is larger than 20 parts by weight, the absorption capacity may be lowered. In the case where the amount of water as used is smaller than 0.5 part by weight, the effects are difficult to appear, and then there is a possibility that the absorption capacity under a load cannot be improved.

In addition, when the water-absorbent resin powder (a) or (a1) is blended with the water-soluble inorganic base (b1) and/or the irreducible alkaline-metal-salt pH buffer (b2) and further with the crosslinking agent (c) or (c1) in the present invention, hydrophilic organic solvents may also be used. Examples of the hydrophilic organic solvents as used include: alcohols, such as methyl alcohol, ethyl alcohol, propyl alcohol, isopropyl alcohol, butyl alcohol, isobutyl alcohol, and t-butyl alcohol; ketones, such as acetone, and methyl ethyl ketone; ethers, such as dioxane, alkoxy(poly) ethylene glycol, and tetrahydrofuran; amides, such as ε-caprolactam, and N,N-dimethylformamide; sulfoxides, such as dimethyl sulfoxide; and polyhydric alcohols, such as ethylene glycol, diethylene glycol, propylene glycol, triethylene glycol, tetraethylene glycol, polyethylene glycol, 1,3-propanediol, dipropylene glycol, 2,2,4-trimethyl-1,3-pentanediol, polypropylene glycol, glycerol, polyglycerol, glycerophosphoric acid, 2-butene-1,4-diol, 1,3-butanediol, 1,4-butanediol, 1,5-pentanediol, 1,6-hexanediol, 1,2-cyclohexanedimethanol, 1,2-cyclohexanol, trimethylolpropane, diethanolamine, triethanolamine, polyoxypropylene, oxyethylene-oxypropylene block copolymers, pentaerythritol, and sorbitol.

The amount of the hydrophilic organic solvent as used is different according to factors such as the kind or particle diameter of the water-absorbent resin, but is usually in the range of 0 to 10 parts by weight, favorably 0 to 5 parts by weight, more favorably 0 to 3 parts by weight, per 100 parts by weight of the water-absorbent resin. In the case where the amount of the hydrophilic organic solvent as used is not smaller than 10 parts by weight, there is a possibility that the solubility of the above additive is lowered and the absorption capacity may not be improved. Incidentally, depending upon reaction conditions (e.g. heating temperature and time, and water content), the above polyhydric alcohol may be used as the crosslinking agent to allow it to react with the water-absorbent resin, or may be used as the solvent without allowing it to react with the water-absorbent resin, or may be used in combinations with their actions.

Furthermore, when the water-absorbent resin powder (a) or (a1) is blended with the water-soluble inorganic base (b1) and/or the irreducible alkaline-metal-salt pH buffer (b2) and further with the crosslinking agent (c) or (c1) in the present invention, surfactants or inert inorganic fine particle powders may be used as substances other than water and the hydrophilic organic solvent in such a range as not to hinder the effects of the present invention. The surfactants or inert inorganic fine particle powders as used are exemplified in gazettes, such as U.S. Pat. No. 5,164,459, EP 827753, EP 349240, and EP 761241.

In the present invention, the blending of the water-absorbent resin powder (a) or (a1) with the water-soluble inorganic base (b1) and/or the irreducible alkaline-metal-salt pH buffer (b2) and further with the crosslinking agent (c) or (c1) may be carried out in a state where this water-absorbent resin is dispersed in an organic solvent such as the hydrophilic organic solvent, cyclohexane or pentane. However, a mixture comprising water, the crosslinking agent, and the additive may be added several divided times, and therefore the blending method is not especially limited. In addition, the water-soluble inorganic base (b1) and/or the irreducible alkaline-metal-salt pH buffer (b2), and further the crosslinking agent (c) or (c1), and further such as water, the hydrophilic organic solvent, and the inorganic powder as used if necessary, may be blended with the water-absorbent resin separately, or in a lump, or several divided times. However, it is favorable that: the water-soluble inorganic base (b1) and/or the irreducible alkaline-metal-salt pH buffer (b2) is beforehand blended with the crosslinking agent (c) or (c1), and thereafter the resultant mixture is added to the water-absorbent resin. In such a case, it is more favorable that the water-soluble inorganic base (b1) and/or the irreducible alkaline-metal-salt pH buffer (b2), and further the crosslinking agent (c) or (c1) are used in a form of an aqueous solution. In addition, in such a case, the temperature of the aqueous solution is controlled in the range of 0° C. to its boiling point, favorably 5 to 50° C., more favorably 10 to 30° C., from the viewpoint of blendability and stability. In addition, the temperature of the water-absorbent resin powder (a) or (a1) is, before the blending, favorably in the range of 0 to 80° C., more favorably 40 to 70° C., from the viewpoint of blendability.

Furthermore, favorable of the various blending methods in the present invention is a method which involves: beforehand blending the water-soluble inorganic base (b1) and/or the irreducible alkaline-metal-salt pH buffer (b2), and further the crosslinking agent (c) or (c1) with water and/or the hydrophilic organic solvent, if necessary; and thereafter spraywise or dropwise, more favorably, spraywise, adding the resultant aqueous solution to the water-absorbent resin powder (a). The size of the liquid drop as sprayed is favorably not larger than 300 μm, more favorably not larger than 200 μm. In addition, when the blending is carried out, water-insoluble fine particle powders or surfactants may coexist in such a range as not to hinder the effects of the present invention.

A favorable blending apparatus as used for the aforementioned blending needs to be able to produce great blending power in order to surely carry out uniform blending. Preferable examples of the blending apparatus usable in the present invention include cylinder type blenders, double-wall cone type blenders, high-speed-stirrer type blenders, V-character-shaped blenders, ribbon type blenders, screw type blenders, fluidized-furnace rotary disk type blenders, air blow type blenders, twin-arm kneaders, internal blenders, pulverizing type kneaders, rotary blenders, and screw type extruders.

The production process for a water-absorbing agent, according to the present invention, is characterized by comprising the step of blending the water-absorbent resin powder (a) or (a1) with the water-soluble inorganic base (b1) and/or the irreducible alkaline-metal-salt pH buffer (b2) and further with the crosslinking agent (c) or (c1), thereby subjecting the water-absorbent resin powder (a) or (a1) to crosslinking treatment.

In the production process for a water-absorbing agent, according to the present invention, it is favorable that: the water-absorbent resin powder (a) or (a1) is blended with the water-soluble inorganic base (b1) and/or the irreducible alkaline-metal-salt pH buffer (b2) and further with the crosslinking agent (c) or (c1), and thereafter the heat treatment is carried out when the surface neighborhood of the water-absorbent resin is crosslinked.

When the heat treatment is carried out in the present invention, the treating time is favorably in the range of 1 to 180 minutes, more favorably in the range of 3 to 120 minutes, still more favorably in the range of 5 to 100 minutes. The heat-treating temperature (as defined by the heat medium temperature or material temperature) is favorably in the range of 100 to 250° C., more favorably 140 to 240° C., still more favorably 150 to 230° C., yet still more favorably 160 to 220° C. In the case where the heating temperature is lower than 100° C., not only the lowering of the productivity is caused because it takes plenty of time to carry out the heat treatment or dehydration reaction, but also an excellent water-absorbing agent may not be obtained because the crosslinking is not uniformly achieved. In addition, in the case where the heating temperature is higher than 250° C., the resultant water-absorbing agent receives damage and therefore there are cases where it is difficult to obtain the water-absorbing agent having excellent properties.

The heat treatment can be carried out with conventional dryers or heating furnaces. Examples thereof include channel type blending dryers, rotary dryers, disk dryers, fluidized-bed dryers, air blow type dryers, and infrared dryers.

The above production process for a water-absorbing agent, according to the present invention, may further comprise a step of giving various functions to the water-absorbing agent or water-absorbent resin, if necessary, such as a step of adding materials such deodorants, antimicrobial agents, perfumes, inorganic powders such as silicon dioxide and titanium oxide, foaming agents, pigments, dyes, hydrophilic short fibers, plasticizers, pressure-sensitive adhesives, surfactants, manure, oxidants, reductants, water, salts, chelating agents, disinfectants, hydrophilic polymers such as polyethylene glycols and polyethylenimine, hydrophobic polymers such as paraffin, thermoplastic resins such as polyethylene and polypropylene, and thermosetting resins such as polyester resins and urea resins. The amount of these additives as used is in the range of 0 to 10 parts by weight, favorably 0 to 1 part by weight, per 100 parts by weight of the water-absorbing agent.

The cationic polymer compound as used for the water-absorbing agent in the present invention can improve such as fixability of the water-absorbing agent to a sanitary material, and favorably has a weight-average molecular weight of not smaller than 2,000, more favorably not smaller than 5,000, most favorably not smaller than 10,000. In addition, the amount as used is favorably in the range of 0.01 to 10 parts by weight, more favorably 0.05 to 5 parts by weight, still more favorably 0.1 to 3 parts by weight, per 100 parts by weight of the water-absorbent resin. The blending of the cationic polymer compound is carried out by adding it alone or in a form of a solution (an aqueous solution), favorably, after surface-crosslinking. Specific examples of the cationic polymer compound include polyethylenimine, polyvinylamine, polyallylamine, condensed products of polyamidamine and epichlorohydrin, polyamidine, partially hydrolyzed products of poly(N-vinylformaldehyde), or their salts.

By using the water-insoluble fine particle, the liquid permeability of the water-absorbing agent and the blocking resistance when absorbing moisture can further be improved. As to the fine particle as used, an inorganic or organic water-insoluble fine particle having a size of favorably not larger than 10 μm, more favorably not larger than 1 μm, particularly favorably not larger than 0.1 μm, is used. Specific examples thereof include silicon oxide (trade name: Aerosil produced by Nippon Aerosil Co., Ltd.), titanium oxide, and aluminum oxide. The blending is carried out by powder-blending (dry-blending) or slurry-blending, and the amount as used is favorably in the range of not larger than 10 parts by weight, more favorably 0.001 to 5 parts by weight, still more favorably 0.01 to 2 parts by weight, per 100 parts by weight of the water-absorbing agent.

(Water-absorbing Agent and Sanitary Material Comprising It):

In the present invention, a novel water-absorbing agent is provided favorably by carrying out a process including the step of blending the water-absorbent resin powder (a) or (a1) with the water-soluble inorganic base (b1) and/or the irreducible alkaline-metal-salt pH buffer (b2) and further with the crosslinking agent (c) or (c1), thereby subjecting the water-absorbent resin powder (a) or (a1) to crosslinking treatment, wherein the novel water-absorbing agent has high properties caused by the aforementioned effects of the present invention.

The water-absorbing agent according to the present invention is favorably a particulate water-absorbing agent of which the major proportion is comprised of a water-absorbent resin that is obtained by a process including the step of polymerizing an unsaturated monomer component and has a crosslinked structure.

(1) Water-absorbing Agent as Obtained When Carrying Out Acid-polymerization:

When the water-absorbent resin is obtained by the acid-polymerization, the water-absorbing agent according to the present invention is favorably a water-absorbing agent obtained by a process including the steps of: polymerizing a monomer including an acid-group-containing monomer (salt); and then post-neutralizing the resultant polymer; and then surface-crosslinking the resultant water-absorbent resin. More favorably, the aforementioned water-absorbent resin resultant from the post-neutralization has a neutralization index of favorably not less than 15, more favorably not less than 17, particularly favorably not less than 20. In addition, the aforementioned surface-crosslinked water-absorbing agent favorably has a neutralization index of not less than 15, more favorably not less than 17, particularly favorably not less than 20. When the neutralization index is decreased so as to enhance surface-crosslinking effects, it takes plenty of time and complicated steps to carry out the neutralization. However, the surface-crosslinking can be achieved easily and excellently in the present invention even if the neutralization is non-uniformly carried out.

Hitherto, a water-absorbent resin, as obtained by a process including the steps of: polymerizing a monomer including an acid-group-containing monomer (salt), and further post-neutralizing the resultant polymer, has had a high absorption capacity and a low extractable content. However, it has been generally difficult to improve an absorption capacity under a load, because the neutralization in the water-absorbent resin as obtained is non-uniform. In order to solve such a problem, known is an art of highly controlling the difference between the neutralization ratios (neutralization indices) of individual particles of water-absorbent resin in JP-A-101735/1998 (EP 0882502).

In the method of controlling this neutralization index, a low-extractable-content-having water-absorbent resin, which was obtained by a process including the steps of: polymerizing a monomer including an acid-group-containing monomer (salt); and further post-neutralizing the resultant polymer, achieved a higher absorption capacity under a load wherein the absorption capacity was not in the past, but it took very much time to control the neutralization index. However, the present invention process, in which the alkaline-metal-salt pH buffer (b2) of the present invention is used, is very favorable because it is unnecessary to highly control the neutralization index, and because the high absorption capacity under a load is given even if the post-neutralization is easily and non-uniformly carried out. Incidentally, needless to say, the present invention is not limited to a low-extractable-content-having water-absorbent resin as obtained by the acid-type polymerization method wherein the water-absorbent resin is obtained by a process including the steps of: polymerizing a monomer including an acid-group-containing monomer (salt); and further post-neutralizing the resultant polymer; but, as is shown in such as the below-mentioned examples, the present invention is favorably applied also to a water-absorbent resin as obtained by a neutralization polymerization method not including the post-neutralization step.

(2) Novel Water-absorbing Agent Having Five Properties Together:

In addition, whether the acid-polymerization is carried out or not, the water-absorbing agent according to the present invention favorably has the following properties. The present invention particularly gives a novel water-absorbing agent having five properties (in addition to the four properties of the particle diameter distribution, CRC, AAP, and SFC, and further at least one (favorably at least two, more favorably at least three, particularly favorably at least four) of such as SFC variation index, SFC variation coefficient, SFC variation rate, SFC standard deviation in a continuous production system, and surface-layer extractable content) together.

(a) Particle Diameter Distribution:

The average particle diameter or bulk density of the water-absorbing agent according to the present invention is favorably in the range of the aforementioned water-absorbent resin, namely, in the range of 300 to 600 µm, wherein the ratio of fine powders having particle diameters of not larger than 150 µm is not more than 10 weight %, more favorably not more than 5 weight %, still more favorably not more than 3 weight %, particularly favorably not more than 2 weight %.

The water-absorbing agent, according to the present invention, includes particles having particle diameters of smaller than 850 µm but not smaller than 150 µm in a ratio of not less than 90 weight % of all particles of the particulate water-absorbing agent, and includes at least two members (favorably at least three members, more favorably four members) selected from the group consisting of: particles (A1) having particle diameters of smaller than 850 µm but not smaller than 600 µm; particles (A2) having particle diameters of smaller than 600 µm but not smaller than 500 µm; particles (A3) having particle diameters of smaller than 500 µm but not smaller than 300 µm; and particles (A4) having particle diameters of smaller than 300 µm but not smaller than 150 µm.

The water-absorbing agent, according to the present invention, favorably includes particles having particle diameters of smaller than 850 µm but not smaller than 150 µm in a ratio of not less than 95 weight %, more favorably not less than 97 weight %, still more favorably not less than 98 weight %, of all the particles. The high properties are achieved in the sanitary material because of controlling to such a specific diameter distribution.

The water-absorbing agent, according to the present invention, favorably includes the aforementioned four kinds of particles A1 to A4 in their respective ratios of not less than 0.1 weight %, more favorably not less than 1 weight %, still more favorably not less than 3 weight %. In this case, the upper limits thereof are not especially limited, but the respective upper limits of the aforementioned four kinds of particles A1 to A4 are favorably not more than 99 weight %, more favorably not more than 90 weight %, still more favorably not more than 80 weight %. The absorption rate, which is dependent upon the surface area of the particle, is controlled in good balance because the water-absorbing agent includes the particles having their respective particle diameter ranges in not less than the definite ratio.

(b) CRC:

The water-absorbing agent, according to the present invention, favorably exhibits a 30 minutes' absorption capacity of not less than 31 g/g without load for a 0.90 weight % physiological saline (Centrifuge Retention Capacity/CRC). Because the CRC becomes not less than 31 g/g, the absorption of the sanitary material comprising the water-absorbing agent is excellent, and the compact sanitary material can be realized, and further it also results in lowering the cost of a water-absorbent structure (incidentally, the water-absorbent structure means a water-absorbent structure for body fluids, comprising the water-absorbing agent, and if necessary, other water-absorbent materials such as fibers). The CRC is more favorably not less than 32 g/g, still more favorably not less than 33 g/g, yet still more favorably not less than 34 g/g, particularly favorably not less than 35 g/g, more particularly favorably not less than 36 g/g. In the case where the 30 minutes' absorption capacity without load for a 0.90 weight % physiological saline is less than 31 g/g, the total amount of urine that can be absorbed by the water-absorbent structure is small, and the amount of the urine as is once absorbed by the water-absorbent structure and then returns to the surface of the disposable diaper is greatly increased. Furthermore, when the absorption amount of the urine as demanded to the water-absorbent structure is designed to be maintained, there are disadvantages in that: the amount of the water-absorbing agent as used for the water-absorbent structure is increased, the sanitary material becomes bulky and heavy, and it results in raising the cost of the water-absorbent structure.

(c) AAP:

The water-absorbing agent, according to the present invention, favorably exhibits a 60 minutes' absorption capacity of not less than 20 g/g under a load of 4.83 kPa for a 0.90 weight % physiological saline (Absorbency Against Pressure/AAP). Because the AAP is not less than 20 g/g, and when the water-absorbing agent according to the present invention is partially used as a water-absorbent structure of disposable diapers, the effect such that the urine as absorbed by the water-absorbent structure is prevented from returning to the surface of the diaper is greatly increased. The 60 minutes' absorption capacity under a load of 4.83 kPa for a 0.90 weight % physiological saline is more favorably not less than 22 g/g, still more favorably not less than 24 g/g, yet still more favorably not less than 25 g/g, particularly favorably not less than 26 g/g, more particularly favorably not less than 27 g/g. In the case where the 60 minutes' absorption capacity under a load of 4.83 kPa for a 0.90 weight % physiological saline is less than 20 g/g, there are disadvantages of greatly decreasing the effect such that the urine as absorbed by the water-absorbent structure is prevented from returning to the surface of the diaper.

(d) SFC:

The water-absorbing agent, according to the present invention, favorably exhibits a saline flow conductivity of not less than 20 (unit: $10^{-7} \times cm^3 \times s \times g^{-1}$) for a 0.69 weight % physiological saline (SFC). The SFC has a very great influence on the liquid permeability of the water-absorbing agent, as obtained in the present invention, after the water-absorbing agent is swollen. That is to say, for example, when the water-absorbing agent according to the present invention is partially used as a water-absorbent structure of disposable diapers, the following effects are remarkably improved: the liquid permeability is improved, and the liquid spreads enough throughout the water-absorbent structure, and the absorption amount of liquid is increased, and the leakage of the liquid is prevented. The SFC is more favorably not less than 25 (unit: $10^{-7} \times cm^3 \times s \times g^{-1}$), still more favorably not less than 30 (unit: $10^{-7} \times cm^3 \times s \times g^{-1}$), yet still more favorably not less than 35 (unit: $10^{-7} \times cm^3 \times s \times g^{-1}$), particularly favorably not less than 40 (unit: $10^{-7} \times cm^3 \times s \times g^{-1}$), more particularly favorably not less than 50 (unit: $10^{-7} \times cm^3 \times s \times g^{-1}$). In the case where the SFC is less than 20 (unit: $10^{-7} \times cm^3 \times s \times g^{-1}$), for example, there are disadvantages in that: when the water-absorbing agent is used as a water-absorbent structure of disposable diapers, the liquid permeability is lowered, and the liquid is localized in the water-absorbent structure, and the absorption amount of liquid is decreased, and the leakage of the liquid is increased, and therefore the properties as the water-absorbent structure are extremely lowered.

That is to say, the water-absorbing agent according to the present invention favorably combines the following three properties in good balance in addition to the particle diameter distribution for the purpose of using it for sanitary materials. That is to say, when only one or two of the CRC, AAP, and SFC were high properties, the water-absorbing agent was found not sufficiently favorable for sanitary materials. These three properties are favorably applied not only to the aforementioned water-absorbing agent being obtained by the acid-polymerization and having a specific neutralization index, but also to a water-absorbent resin as obtained by the neutralization polymerization not including the post-neutralization step.

A 30 minutes' absorption capacity of not less than 31 g/g without load for a 0.90 weight % physiological saline (CRC).

A 60 minutes' absorption capacity of not less than 24 g/g under a load of 4.83 kPa for a 0.90 weight % physiological saline (AAP).

A saline flow conductivity of not less than 20 (unit: $10^{-7} \times cm^3 \times s \times g^{-1}$) for a 0.69 weight % physiological saline (SFC).

(e) SFC Variation Index:

In addition, the present inventors have found out a fact that: in water-absorbent resin (water-absorbing agent) particles of which the properties have hitherto been evaluated and managed as the entirety of the particles (Bulk), the properties of the water-absorbent resin (water-absorbing agent) particles are greatly different according to their particle diameters, and this difference of the properties according to particle diameters causes the lowering of the properties in sanitary materials. It is presumed that the scatter of the particle diameters is microscopically seen in the water-absorbing agent particles as included in the sanitary materials, and therefore the difference of the properties according to individual sanitary materials or according to parts of one sanitary material, as based on the particle diameter distribution; causes the lowering of the properties in the sanitary materials.

Thus, the present inventors provide a water-absorbing agent having little difference of properties according to particle diameters, especially little scatter of SFC according to particle diameters.

The water-absorbing agent, according to the present invention, favorably has an SFC variation index of 0 to 25% wherein the SFC variation index is defined by the following equation (1):

$$SFC \text{ variation index } (\%) = [(\text{standard deviation of } SFCs \text{ of particles } A1 \text{ to } A4)/(SFC \text{ of entire particulate water-absorbing agent})] \times 100 \quad (1).$$

In this SFC variation index and the following SFC variation coefficient, the standard deviation of SFCs of the particles A1 to A4 is determined by classifying the water-absorbing agent particles to obtain 2 to 4 kinds of particles existing among the particles A1 to A4 in the water-absorbing agent, and subsequently measuring the SFCs of the resultant particles in their respective particle diameter ranges one time each, and then calculating the standard deviation from the SFC values of the 2 to 4 kinds of particles. In addition, the average value is also calculated in the same way from the SFC values of the 2 to 4 kinds of particles.

This SFC variation index represents the scatter of the SFCs according to particle diameters. When the SFC variation index is in the range of 0 to 25%, the following effects are obtained: the water-absorbent structure has more uniform liquid permeability, and the liquid easily disperses into the entire water-absorbent structure, and the leakage of the liquid is prevented. The SFC variation index is more favorably in the range of 0 to 23%, still more favorably in the range of 0 to 20%, yet still more favorably in the range of 0 to 18%, particularly favorably in the range of 0 to 15%, more particularly favorably in the range of 0 to 10%. In the case where the SFC variation index is more than 25%, for example, there are disadvantages in that: when the water-absorbing agent is used for a water-absorbent structure of disposable diapers, the scatter of liquid permeability is caused in the water-absorbent structure, and it becomes difficult to disperse the liquid into the entire water-absorbent structure, and the leakage of the liquid is caused, and the liquid absorption amount of the water-absorbent structure is decreased.

(f) SFC Variation Coefficient:

The water-absorbing agent, according to the present invention, favorably has an SFC variation coefficient of 0 to 0.25, wherein the SFC variation coefficient is defined by the following equation (2):

$$SFC \text{ variation coefficient} = (\text{standard deviation of } SFCs \text{ of particles } A1 \text{ to } A4)/(\text{average of } SFCs \text{ of particles } A1 \text{ to } A4) \quad (2).$$

This SFC variation coefficient and the following SFC variation rate also similarly represent littleness of the difference of the SFCs according to particle diameters. When the SFC variation coefficient is in the range of 0 to 0.25, the extent of the scatter of the SFCs according to particle diameters (for example, A1 to A4) is lowered. For example, when a water-absorbent structure of disposable diapers is produced using the water-absorbing agent according to the present invention, the liquid permeability is uniform in the water-absorbent structure, and further the scatter of performance of the disposable diapers disappears even if water-absorbent structures are compared with each other, and it results in enabling to produce disposable diapers having stable qualities. The SFC variation coefficient is more favorably in the range of 0 to 0.23, still more favorably in the range of 0 to 0.20, yet still more favorably in the range of 0 to 0.18, particularly favorably in the range of 0 to 0.15, more particularly favorably in the range of 0 to 0.10. In the case where the SFC variation coefficient is more than 0.25 and/or where the SFC variation rate is less than 0.65, there are disadvantages in that: the liquid permeability is non-uniform in the water-absorbent structure of the sanitary material (especially, disposal diapers) comprising the water-absorbing agent, and further the scatter of performance of the disposable diapers is increased even if water-absorbent structures are compared with each other, and therefore disposable diapers having stable qualities cannot be produced.

(g) SFC Variation Rate:

The water-absorbing agent, according to the present invention, favorably has an SFC variation rate of 0.65 to 1.00, wherein the SFC variation rate is defined by the following equation (3):

$$SFC \text{ variation rate} = (\text{minimum } SFC \text{ among } SFCs \text{ of particles } A1 \text{ to } A4)/(\text{maximum } SFC \text{ among } SFCs \text{ of particles } A1 \text{ to } A4) \quad (3).$$

This SFC variation rate also similarly represent littleness of the difference of the SFCs according to particle diameters, and is more favorably in the range of 0.70 to 1.00, still more favorably 0.75 to 1.00, particularly favorably 0.80 to 1.00.

(h) Surface-layer Extractable Content:

The water-absorbing agent, according to the present invention, favorably has a surface-layer extractable content of not more than 6.0 weight % (based on the water-absorbing agent). This surface-layer extractable content is favorably not more than 5.5 weight %, more favorably not more than 5.0 weight %, still more favorably not more than 4.5 weight %, particularly favorably not more than 4.0 weight %.

The surface-layer extractable content as determined by the measurement method of the present invention means an extractable content corresponding to the practical use for the sanitary material, and the water-absorbing agent has more excellent absorbency in the sanitary material. That is to say, a lot of measurements of the water-extractable content (e.g. U.S. Pat. No. Re 32,649 and EDANA method) have been known hitherto. However, it has been found out that, hitherto, a larger excess of the extractable content was measured than the extractable content as thought to elute in the practical use because the measurement was carried out in an excess of liquid for a long time. Then, the method of the present invention has been found to be the best model for the practical use in the sanitary material.

(i) SFC Standard Deviation in a Continuous Production System:

The water-absorbing agent, according to the present invention, favorably has an SFC standard deviation of not more than 5.0 in a continuous production system, wherein the SFC standard deviation in a continuous production system is defined by the following equation (4):

$$SFC \text{ standard deviation in a continuous production system} = \text{standard deviation of } SFC \text{ of each lot} \quad (4)$$

where: each lot has a weight of not less than 20 kg; and the number of the lots is not smaller than 10.

The above continuous production system means continuously producing a water-absorbing agent for not less than 24 hours or in an amount of not smaller than 10 tons, per one line. In addition, as to fundamental steps of the production process for a water-absorbing agent (e.g. polymerization, drying, pulverization, and surface treatment), each step is carried out at an interval of not more than 24 hours (favorably not more than 12 hours, more favorably not more than 6 hours, particularly favorably not more than 3 hours) in the continuous production system, regardless of a continuous manner or batchwise manner (e.g. continuous polymerization or batchwise polymerization in a polymerization step).

Each lot favorably has a weight of 20 kg to 100 tons, more favorably 0.1 to 50 tons, still more favorably 0.5 to 25 tons.

The number of the lots is favorably not smaller than 20, more favorably not smaller than 30, still more favorably not smaller than 50, particularly favorably not smaller than 100.

This SFC standard deviation in a continuous production system represents the scatter of the SFC values among lots. When the SFC standard deviation in a continuous production system is not more than 5.0, the scatter of the SFC values among lots is lowered. For example, when a water-absorbent structure of disposable diapers is produced using the water-absorbing agent according to the present invention, it results in enabling to produce disposable diapers having stable qualities. The SFC standard deviation in a continuous production system is more favorably not more than 4.5, still more favorably not more than 4.3, yet still more favorably not more than 4.0, particularly favorably 3.5, more particularly favorably 3.0, most favorably not more than 2.5. In the case where the SFC standard deviation in a continuous production system is more than 5.0, there are disadvantages in that disposable diapers having stable qualities cannot be produced.

Incidentally, in the case where the water-absorbing agent is used for sanitary materials, the above various properties are important properties that are mutually related with results (e.g. absorption quantity and leakage of diapers) of the practical use, and the water-absorbing agent according to the present invention is particularly excellent in the above various properties. Their measurement methods are described in the "DETAILED DESCRIPTION OF THE PREFERRED EMBODIMENTS" portion hereof.

The water-absorbing agent, according to the present invention, favorably has the various characters as mentioned above. The water-absorbing agent having particularly favorable constitution is a water-absorbing agent that satisfies at least one (more favorably at least two, still more favorably all three) of the above equations (1), (2), and (4).

That is to say, a water-absorbing agent, according to the present invention, is a particulate water-absorbing agent of which the major proportion is comprised of a water-absorbent resin that is obtained by a process including the step of polymerizing an unsaturated monomer component and has a crosslinked structure, with the water-absorbing agent being characterized in that: the particulate water-absorbing agent includes particles having particle diameters of smaller than 850 μm but not smaller than 150 μm in a ratio of not less than 90 weight % of all particles of the particulate water-absorbing agent; and includes at least two members selected from the group consisting of: particles (A1) having particle diameters of smaller than 850 μm but not smaller than 600 μm; particles (A2) having particle diameters of smaller than 600 μm but not smaller than 500 μm; particles (A3) having particle diameters of smaller than 500 μm but not smaller than 300 μm; and particles (A4) having particle diameters of smaller than 300 μm but not smaller than 150 μm; and further satisfies the following properties:

a 30 minutes' absorption capacity of not less than 31 g/g without load for a 0.90 weight % physiological saline (CRC);

a 60 minutes' absorption capacity of not less than 24 g/g under a load of 4.83 kPa for a 0.90 weight % physiological saline (AAP);

a saline flow conductivity of not less than 20 (unit: $10^{-7} \times cm^3 \times s \times g^{-1}$) for a 0.69 weight % physiological saline (SFC); and an SFC variation index of 0 to 25% wherein the SFC variation index is defined by the following equation (1):

$$SFC \text{ variation index } (\%) = [(\text{standard deviation of } SFCs \text{ of particles } A1 \text{ to } A4)/(SFC \text{ of entire particulate water-absorbing agent})] \times 100 \qquad (1).$$

In addition, another water-absorbing agent, according to the present invention, is a particulate water-absorbing agent of which the major proportion is comprised of a water-absorbent resin that is obtained by a process including the step of polymerizing an unsaturated monomer component and has a crosslinked structure, with the water-absorbing agent being characterized in that: the particulate water-absorbing agent includes particles having particle diameters of smaller than 850 μm but not smaller than 150 μm in a ratio of not less than 90 weight % of all particles of the particulate water-absorbing agent; and includes at least two members selected from the group consisting of: particles (A1) having particle diameters of smaller than 850 μm but not smaller than 600 μm; particles (A2) having particle diameters of smaller than 600 μm but not smaller than 500 μm; particles (A3) having particle diameters of smaller than 500 μm but not smaller than 300 μm; and particles (A4) having particle diameters of smaller than 300 μm but not smaller than 150 μm; and further satisfies the following properties:

a 30 minutes' absorption capacity of not less than 31 g/g without load for a 0.90 weight % physiological saline (CRC);

a 60 minutes' absorption capacity of not less than 24 g/g under a load of 4.83 kPa for a 0.90 weight % physiological saline (AAP);

a saline flow conductivity of not less than 20 (unit: $10^{-7} \times cm^3 \times s \times g^{-1}$) for a 0.69 weight % physiological saline (SFC); and an SFC variation coefficient of 0 to 0.25, wherein the SFC variation coefficient is defined by the following equation (2):

$$SFC \text{ variation coefficient} = (\text{standard deviation of } SFCs \text{ of particles } A1 \text{ to } A4)/(\text{average of } SFCs \text{ of particles } A1 \text{ to } A4) \qquad (2).$$

In addition, yet another continuously produced water-absorbing agent, according to the present invention, is a particulate water-absorbing agent of which the major proportion is comprised of a water-absorbent resin that is obtained by a process including the step of polymerizing an unsaturated monomer component and has a crosslinked structure, with the water-absorbing agent being characterized in that: the particulate water-absorbing agent includes particles having particle diameters of smaller than 850 μm but not smaller than 150 μm in a ratio of not less than 90 weight % of all particles of the particulate water-absorbing agent; and includes at least two members selected from the group consisting of: particles (A1) having particle diameters of smaller than 850 μm but not smaller than 600 μm; particles (A2) having particle diameters of smaller than 600 μm but not smaller than 500 μm; particles (A3) having particle diameters of smaller than 500 μm but not smaller than 300 μm; and particles (A4) having particle diameters of smaller than 300 μm but not smaller than 150 μm; and further satisfies the following properties:

a 30 minutes' absorption capacity of not less than 31 g/g without load for a 0.90 weight % physiological saline (CRC);

a 60 minutes' absorption capacity of not less than 24 g/g under a load of 4.83 kPa for a 0.90 weight % physiological saline (AAP);

a saline flow conductivity of not less than 20 (unit: $10^{-7} \times cm^3 \times s \times g^{-1}$) for a 0.69 weight % physiological saline (SFC); and an SFC standard deviation of not more than 5.0 in a continuous production system, wherein the SFC standard deviation in a continuous production system is defined by the following equation (4):

$$SFC \text{ standard deviation in a continuous production system} = \text{standard deviation of } SFC \text{ of each lot} \qquad (4)$$

where: the CRC, AAP, and SFC are on average of the lots; each lot has a weight of not less than 20 kg; and the number of the lots is not smaller than 10.

Yet another water-absorbing agent, according to the present invention, is a particulate water-absorbing agent obtained by a process including the steps of: polymerizing a monomer including an acid-group-containing monomer (salt); and then post-neutralizing the resultant polymer; and then surface-crosslinking the resultant water-absorbent resin, with the water-absorbing agent being characterized in that the particulate water-absorbing agent or the water-absorbent resin has a neutralization index of not less than 15 and exhibits a 60 minutes' absorption capacity of not less than 20 g/g under a load of 4.83 kPa for a 0.90 weight % physiological saline (AAP) after the surface-crosslinking.

In the above water-absorbing agent, the CRC, AAP, SFC, SFC variation index, and SFC variation coefficient are favorably in the aforementioned range, and the novel water-absorbing agent according to the present invention, is for example, obtained by the aforementioned production process for a water-absorbing agent according to the present invention. In the water-absorbing agent according to the present invention, the CRC, AAP, and SFC are very high, and the high properties are maintained in good balance, and further the variation of the properties according to particle diameters is also less than conventional. Therefore, the water-absorbing agent is an excellent water-absorbing agent that displays high properties under any condition of using the sanitary material.

According to the present invention, the water-absorbing agent, which is excellent in balance of an absorption capacity without load, an absorption capacity under a load, and a saline flow conductivity, and which has good absorption properties, can easily be produced, and it is widely used for such as water-holding agents for agricultural and horticultural fields, industrial water-holding agents, moisture-absorbing agents, moisture-removing agents, and building materials. However, the water-absorbing agent can particularly favorably be used for sanitary materials for absorbing feces, urine, or blood, such as disposable diapers and sanitary napkins. Furthermore, the water-absorbing agent according to the present invention is excellent in the balance of the above various properties, and therefore the sanitary material can generally be used in a high concentration as a concentration of the water-absorbing agent (weight ratio of water-absorbing agent to the total of water-absorbing agent and fibrous base material), for example, in the range of 30 to 100 weight %, favorably 40 to 100 weight %, more favorably 50 to 95 weight %. In addition, the structure of the water-absorbent structure in the sanitary material is not especially limited if it is a structure used for a general water-absorbent article. Examples thereof include: water-absorbent structures obtained by placing the water-absorbing agent between hydrophilic fiber materials, and then molding them into sheets, namely, water-absorbent structures having sandwich structures; and water-absorbent structures obtained by molding a mixture of a hydrophilic fiber material and the water-absorbing agent, namely, water-absorbent structures having blended structures.

DETAILED DESCRIPTION OF THE PREFERRED EMBODIMENTS

Hereinafter, the present invention is more specifically illustrated by the following examples of some preferred embodiments in comparison with comparative examples not according to the invention. However, the invention is not limited to these examples. Incidentally, the various performances of the water-absorbent resins or water-absorbing agents were measured by the following methods.

Incidentally, in cases of water-absorbing agents having been used for end products such as sanitary materials, the water-absorbing agents have already absorbed moisture. Therefore, the measurements may be carried out after fitly separating the water-absorbing agents from the end products and drying them under a reduced pressure at a low temperature (e.g. under not higher than 1 mmHg at 60° C. for 12 hours). In addition, all the water-absorbent resins as used in Examples and Comparative Examples of the present invention have water contents of not larger than 6 weight %.

Furthermore, when the SFCs according to particle diameters are measured in the following (4), the SFCs of the water-absorbing agents having been used for end products (e.g. sanitary materials) are measured after the above operation. However, when unused water-absorbing agents, namely, water-absorbing agents intact after being produced in a laboratory, are measured, such water-absorbing agents are, on all occasions, subjected to the mechanical damage of the below-mentioned (5) and thereafter measured by the SFCs according to particle diameters and the SFCs of unclassified particles, in order to correlate them with the damage of the practical production or use.

(1) Absorption Capacity Without Load (30 Minutes' Absorption Capacity Without Load for a 0.90 Weight % Physiological Saline/CRC):

Under conditions of a room temperature (20 to 25° C.) and a relative humidity of 50%, 0.20 g of water-absorbent resin or water-absorbing agent was uniformly added to a nonwoven-fabric-made bag (60 mm×60 mm), and then the bag was sealed. Thereafter, the bag was immersed into a 0.9 weight % physiological saline at room temperature. The bag was pulled up after 30 minutes, and the weight ($W1(g)$) of the bag was measured after draining water off at 250 G for 3 minutes with a centrifugal separator (produced by Kokusan Co., Ltd., centrifugal separator: model type H-122). In addition, the same procedure was carried out without using any water-absorbing agent or water-absorbing agent, and then the weight ($W0(g)$) of the bag was measured. Then, the absorption capacity (g/g) without load was calculated from these W0 and W1 in accordance with the following equation:

$$\text{absorption capacity (g/g) without load} = (W1(g) - W0(g))/\text{weight (g) of water-absorbent resin or water-absorbing agent}$$

(2) Absorption Capacity Under a Load (60 Minutes' Absorption Capacity Under a Load of 4.83 kPa for a 0.90 Weight % Physiological Saline/AAP):

Under conditions of a room temperature (20 to 25° C.) and a relative humidity of 50%; 0.90 g of water-absorbing agent was uniformly spread on a stainless wire net of 400 mesh (mesh opening size: 38 μm) as attached by fusion to the bottom of a plastic supporting cylinder of an inner diameter 60 mm, on which a piston and a load were further mounted in sequence, wherein: the piston had an outer diameter only a little smaller than 60 mm and made no gap with the wall face of the supporting cylinder, but was not hindered from moving up and down, and the total weight of the piston and the load were adjusted to uniformly apply a load of 4.83 kPa (0.7 psi) to the water-absorbent agent. Then, the weight ($Wa(g)$) of the resultant set of measurement apparatus was measured.

A glass filter of 90 mm in diameter (produced by Sogo Rikagaku Glass Seisakusho Co., Ltd, pore diameter: 100 to 120 μm) was mounted inside a Petri dish having a diameter of 150 mm, and a 0.90 weight % physiological saline (20 to 25° C.) was added up to the same level as the upper surface of the glass filter, on which a filter paper having a diameter of 90 mm (produced by ADVANTEC Toyo Co., Ltd., trade name: (JIS P 3801, No. 2), thickness: 0.26 mm, and diameter of captured particles: 5 μm) was then mounted such that its entire surface would be wetted, and the excessive liquid was removed.

The above set of measurement apparatus was mounted on the above wet filter paper, thereby allowing the water-absorbing agent to absorb the liquid under a load. After 1 hour, the set of measurement apparatus was lifted, and its weight (Wb(g)) was measured. Then, the absorption capacity (g/g) under a load was calculated from these Wa and Wb in accordance with the following equation:

absorption capacity (g/g) under a load=(Wa(g)−Wb(g))/weight of water-absorbing agent ((0.9)g)

(3) Weight-average Particle Diameter:

Water-absorbent resin powders or water-absorbing agents were classified with JIS standard sieves having mesh opening sizes of such as 850 μm, 600 μm, 500 μm, 425 μm, 300 μm, 212 μm, 150 μm, 106 μm, and 75 μm, and then the percentages of the residues R on these sieves were plotted on logarithmic probability paper. Therefrom, the weight-average particle diameter (D50) was read.

As to the classifying method when the classification is carried out and the below-mentioned SFCs according to particle diameters are measured, 10.0 g of water-absorbent resin powder or water-absorbing agent was added to JIS standard sieves (THE IIDA TESTING SIEVE having a diameter of 8 cm) having mesh opening sizes of 850 μm, 600 μm, 500 μm, 300 μm, and 150 μm under conditions of a room temperature (20 to 25° C.) and a relative humidity of 50%, and then classified with a sieve shaker (IIDA SIEVE SHAKER, TYPE: ES-65 type, SER. No. 0501) for 10 minutes.

(4) Saline Flow Conductivity for a 0.69 Weight % Physiological Saline (SFC):

The following test was carried out according to the saline flow conductivity (SFC) test as described in JP-A-509591/1997.

An apparatus as shown in FIG. 1 is used, and a water-absorbing agent (0.900 g) as uniformly added to a receptacle 40 is swollen in artificial urine (1) for 60 minutes under a load of 0.3 psi (2.07 kPa), and the gel layer height of the resultant gel 44 is recorded. Next, under the load of 0.3 psi (2.07 kPa), a 0.69 weight % physiological saline 33 is passed through the swollen gel layer from a tank 31 under a constant hydrostatic pressure. This SFC test was carried out at room temperature (20 to 25° C.). The amount of the liquid passing through the gel layer versus time is recorded as a function to time with a computer and a balance at twenty seconds' intervals for 10 minutes. The flow rate through the swollen gel 44 (mainly between particles thereof), $F_s(t)$, is determined in a unit of g/s by dividing the incremental weight (g) by incremental time (s). The time when the constant hydrostatic pressure and the stable flow rate are obtained is regarded as $t_s$, and only the data collected for times between $t_s$ and 10 minutes are used for flow rate calculations. $F_s$ (t=0) value, namely, the initial flow rate through the gel layer, is calculated from the flow rate between $t_s$ and 10 minutes. $F_s$ (t=0) is calculated by extrapolating the results of a least-squares fit of $F_s$ (t) versus time to t=0.

$$\text{Saline flow conductivity} = (F_s(t=0) \times L_0)/(\rho \times A \times \Delta P)$$
$$= (F_s(t=0) \times L_0)/139{,}506$$

where:

$F_s$ (t=0): flow rate in g/sec;

$L_0$: initial thickness of gel layer in cm;

ρ: density of NaCl solution (1.003 g/cm$^3$);

A: area of the upper side of gel layer in the cell 41 (28.27 cm$^2$);

ΔP: hydrostatic pressure applied to gel layer (4,920 dyne/cm$^2$); and the unit of the SFC value is: $10^{-7} \times cm^3 \times s \times g^{-1}$.

As to the apparatus as shown in FIG. 1, a glass tube 32 is inserted into the tank 31, and the lower end of the glass tube 32 was arranged so that the 0.69 weight % physiological saline 33 could be maintained at a height of 5 cm from the bottom of the swollen gel 44 in a cell 41. The 0.69 weight % physiological saline 33 in the tank 31 was supplied to the cell 41 through a L-tube 34 having a cock. A receptacle 48 to collect the passed liquid was arranged under the cell 41, and the collecting receptacle 48 was arranged on a balance 49. The inner diameter of the cell 41 was 6 cm, and a No. 400 stainless wire mesh 42 (mesh opening size of 38 μm) was arranged at the bottom thereof. Holes 47 sufficient for the liquid to pass through were opened in the lower portion of a piston 46, and its bottom portion was equipped with a permeable glass filter 45 so that the water-absorbing agent or its swollen gel would not enter the holes 47. The cell 41 was placed on a stand to put the cell thereon. The face, coming in contact with the cell, of the stand was arranged on a stainless wire mesh 43 that did not inhibit liquid permeation.

The artificial urine (I) as used was obtained by adding: 0.25 g calcium chloride dihydrate; 2.0 g of potassium chloride; 0.50 g of magnesium chloride hexahydrate; 2.0 g of sodium sulfate; 0.85 g of ammonium dihydrogenphosphate; 0.15 g of diammonium hydrogenphosphate; and 994.25 g of pure water.

Figure 2:
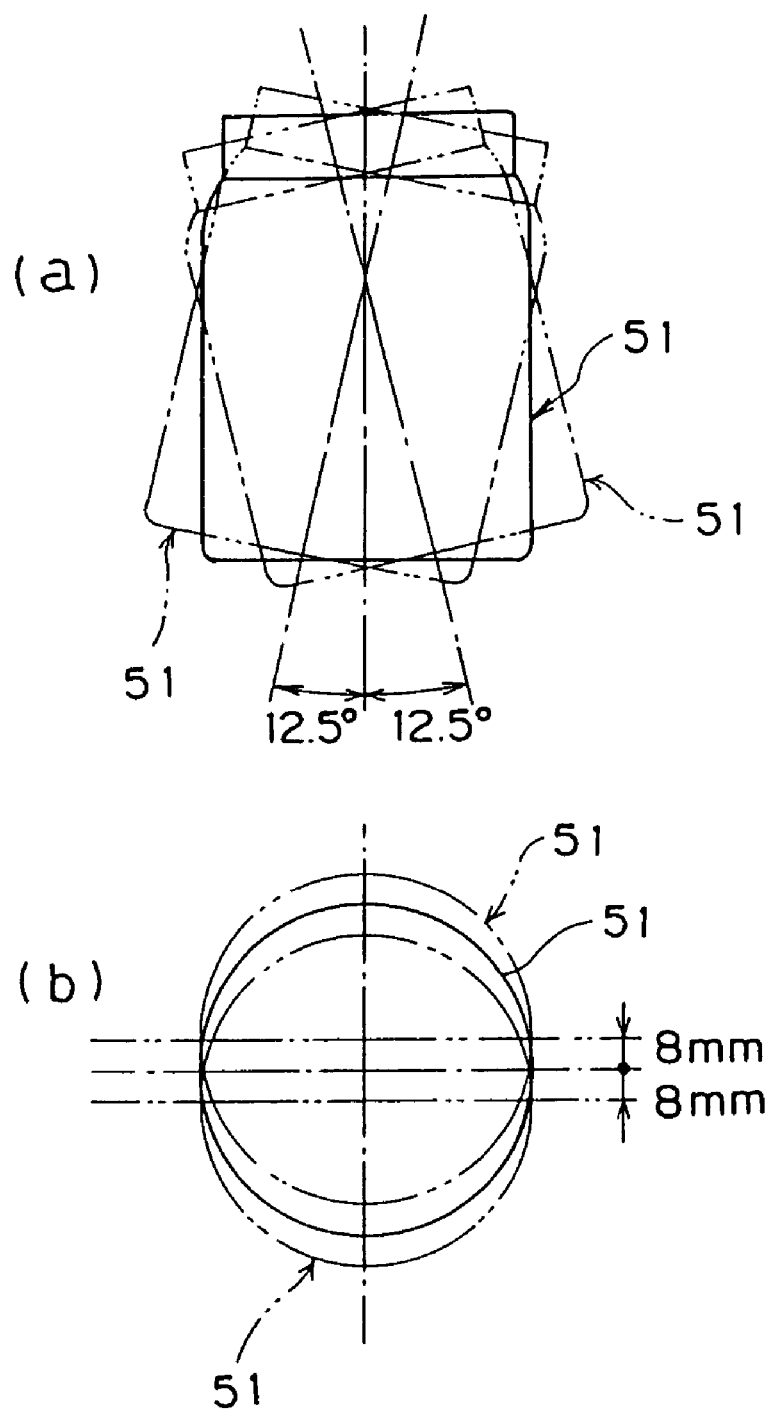
FIG. 2 is a schematic side-view (a) and a schematic planar-view (b) of a glass-made receptacle as used for a mechanical damage test.
Figure 3:
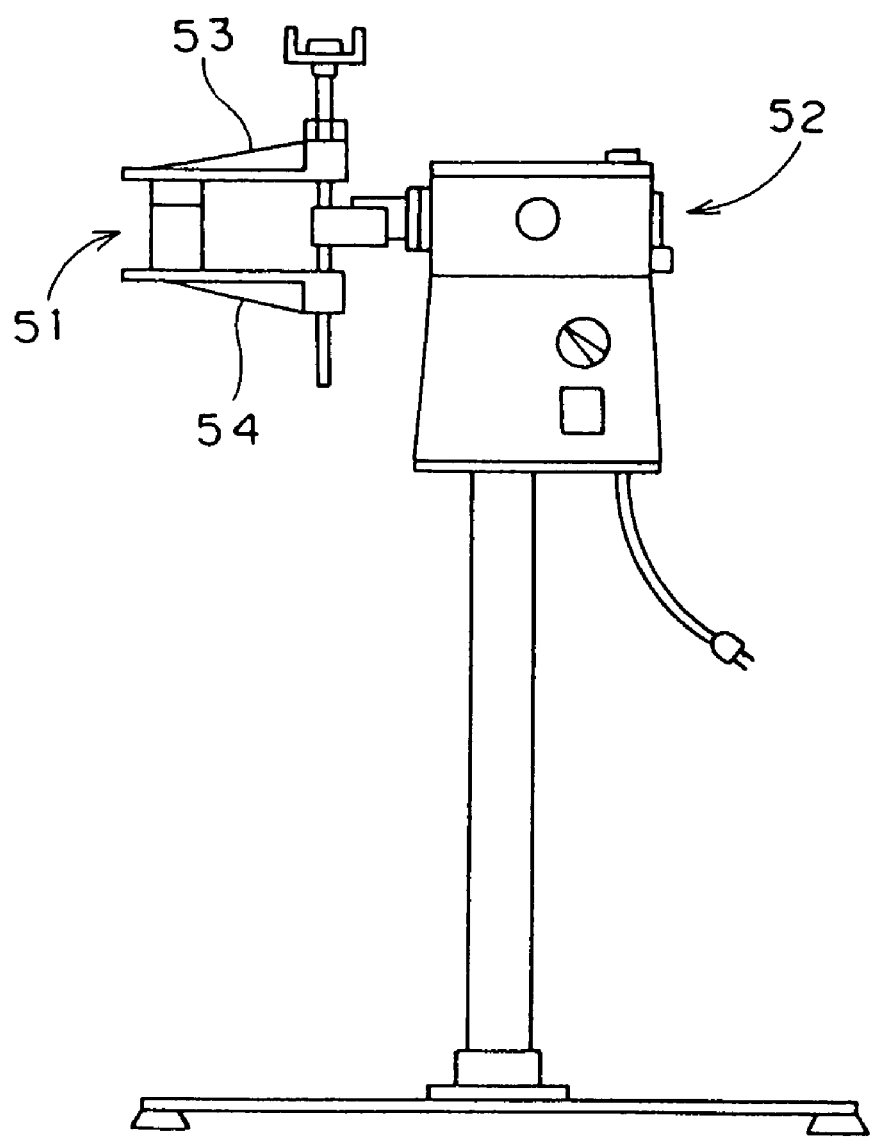
FIG. 3 is a schematic view of a disperser as used for the mechanical damage test.

(5) Mechanical Damage Test:

To a glass-made receptacle (mayonnaise bottle produced by Yamamura Glass Co., Ltd., trade name: A-29) as shown in FIG. 2, there were added 30 g of water-absorbing agent and 10 g of glass beads (soda-lime glass beads for pack rectification with a bead diameter of about 6 mm). This receptacle was put and fixed between clamps which was equipped to a disperser (produced by Toyo Seiki Seisakusho Co., Ltd., No. 488 test disperser) as shown in FIG. 3, and then this receptacle was vibrated at the number of vibrational revolutions of 750 cpm by 100 V/60 Hz for 10 minutes. Thereby, the receptacle as fixed to the above disperser is slope-moved right and left by 12.5° each (25° in total) to the attached face to the above clamps of the disperser, and is vibrated back and forth by 8 mm each (16 mm in total) at the same time. Therefore, a shock is given to the water-absorbing agent in the receptacle. The above shock is an experientially determined power as a representative of impact that the water-absorbing agent receives in its production process, but it is also widely applied to damage as caused when the water-absorbing agent is transported after the production, and when water-absorbent structures are produced. When the mechanical damage is caused in the present invention, there is assumed especially when a water-absorbing agent or water-absorbent structure is produced. Furthermore, the SFC variation index, SFC variation coefficient, and SFC variation rate are indices for measuring the scatter of performance of the water-absorbing agent in the water-absorbent structure. Therefore, when the measurement of properties according to particle diameters is carried out, the aforementioned mechanical damage has to be caused to all the water-absorbing agents as produced in a laboratory scale (the amount of the water-absorbing agent as obtained in one production process is not larger than 20 kg.).

(6) Extractable (Water-extractable) Content:

Into a plastic receptacle of 250 ml in capacity having a lid, 184.3 g of 0.9 weight % aqueous physiological sodium chloride solution (physiological saline) was weighed out. Then, 1.00 g of water-absorbent resin was added to the aqueous solution, and they were stirred for 16 hours, thereby the extractable content in the resin was extracted. This extract liquid was filtrated with a filter paper (produced by ADVANTEC Toyo Co., Ltd., trade name: (JIS P 3801, No. 2), thickness: 0.26 mm, and diameter of captured particles: 5 μm), and then 50.0 g of the resultant filtrate was weighed out and regarded as a measuring solution.

To begin with, only the physiological saline was firstly titrated with an aqueous 0.1N NaOH solution until the pH reached 10, and then the resultant solution was titrated with an aqueous 0.1N HCl solution until the pH reached 2.7, thus obtaining blank titration amounts ([bNaOH] ml and [bHCl] ml).

The same titration procedure was carried out for the measuring solution, thus obtaining titration amounts ([NaOH] ml and [HCl] ml).

For example, if the water-absorbent resin comprises acrylic acid and its sodium salt in known amounts, the extractable content of the water-absorbent resin can be calculated from the average molecular weight of the monomers and the titration amounts, as obtained from the above procedures, in accordance with the following equation. In the case of unknown amounts, the average molecular weight of the monomers is calculated by the neutralization ratio as determined by the titration.

extractable content (weight %)=0.1×(average molecular weight)×184.3×100×([HCl]−[bHCl])/1,000/1.0/50.0 neutralization ratio (mol %)=(1−([NaOH]−[bNaOH])/([HCl]−[bHCl]))×100

(7) Surface-layer Extractable (Water-extractable) Content:

Into a plastic receptacle of 250 ml in capacity having a lid, 100 g of 0.50 weight % aqueous physiological sodium chloride solution was weighed out. Then, 0.50 g of water-absorbing agent was added to the aqueous solution, and the surface-layer extractable content in the water-absorbing agent was extracted for 1 hour. In this extracting operation, the stirring is carried out for the purposes of only dispersing the water-absorbing agent at the initial stage and rendering the resultant final liquid uniform, but otherwise the stirring is not carried out. Particularly, the extraction of the surface-layer extractable content is carried out under static conditions, and the stirring (rotating speed: 400 r.p.m, stirring rotator made of Teflon (2.5 cm)) is carried out for only 1 minute before and after the extraction. This extract liquid was filtrated with a filter paper (produced by ADVANTEC Toyo Co., Ltd., trade name: (JIS P 3801, No. 2), thickness: 0.26 mm, and diameter of captured particles: 5 μm), and then 50.0 g of the resultant filtrate was weighed out and regarded as a measuring solution.

To begin with, only the 0.5 weight % aqueous NaCl solution was firstly titrated with an aqueous 0.1N NaOH solution until the pH reached 10, and then the resultant solution was titrated with an aqueous 0.1N HCl solution until the pH reached 2.7, thus obtaining blank titration amounts ([bNaOH] ml and [bHCl] ml).

The same titration procedure was carried out for the measuring solution, thus obtaining titration amounts ([NaOH] ml and [HCl] ml).

For example, if the water-absorbing agent comprises acrylic acid and its sodium salt in known amounts, the surface-layer extractable content of the water-absorbing agent can be calculated from the average molecular weight of the monomers and the titration amounts, as obtained from the above procedures, in accordance with the following equation. In the case of unknown amounts, the average molecular weight of the monomers is calculated by the neutralization ratio as determined by the titration.

surface-layer extractable content (weight %)=0.1×(average molecular weight)×100×100×([HCl]−[bHCl])/1,000/0.50/50.0 neutralization ratio (mol %)=(1−([NaOH]−[bNaOH])/([HCl]−[bHCl]))×100

(8) Neutralization Index:

The neutralization indices of the water-absorbent resin powder and water-absorbing agent were determined in accordance with JP-A-101735/1998 and claim 3 therein (EP 0882502 and claims 2 to 4 therein).

That is to say, 200 particles of water-absorbent resin powder or water-absorbing agent as classified into 300 μm to 600 μm with JIS standard sieves are added to a plastic plate with a cover glass attached thereto wherein the plastic plate has a thickness of 1.6 mm and is provided with an opening section with a size of 20 mm×20 mm. Then, 0.2 ml of deionized water is added thereto. Furthermore, 0.05 ml of mixed solution of 0.1 weight % ethanolic bromothimol blue (BTB) solution and 0.1 weight % ethanolic methyl red (MR) solution in a ratio of 1.5 to 1 was added to the above swollen gel with a micro syringe, and then the coloring of the 200 particles was observed by the pH indicators. In this way determined were the number of particles (how many of the 200 particles) that were non-uniformly neutralized and had neutralization ratios more than the average neutralization ratio of the water-absorbent resin or water-absorbing agent by more than 20 mol % to determine the number of these non-uniformly neutralized particles as the neutralization index (first neutralization index in the above patent/claim 3). Needless to say, the larger the neutralization index is, the more non-uniform the neutralization of the water-absorbent resin powder is. For details, refer to the above patent.

REFERENTIAL EXAMPLE 1

Production Example of Water-absorbent Resin Powder (A)/Neutralization Polymerization In a reactor as prepared by lidding a jacketed stainless twin-arm kneader of 10 liters in capacity with two sigma-type blades, a reaction liquid was obtained by dissolving 3.70 g of polyethylene glycol diacrylate (n=9) into 5,500 g of aqueous sodium acrylate solution having a neutralization ratio of 75 mol % (monomer concentration: 38 weight %, and average molecular weight of monomer: 88.5). Next, this reaction liquid was deaerated under an atmosphere of nitrogen for 30 minutes. Subsequently, 28.3 g of 10 weight % aqueous sodium persulfate solution and 2.1 g of 1 weight % aqueous L-ascorbic acid solution were added thereto under stirred conditions. As a result, the reaction was started after about one minute. Then, the polymerization was carried out at 20 to 95° C. while the resultant formed gel was pulverized, and the resultant crosslinked hydrogel polymer (1) was taken out after 30 minutes from the start of the polymerization.

The crosslinked hydrogel polymer (1) as obtained was in finely divided pieces having a diameter of not larger than about 5 mm. This finely divided crosslinked hydrogel polymer (1) was spread on a metal gauze with 50 mesh (a mesh opening size of 300 μm), and hot-wind-dried at 150° C. for 90 minutes. Next, the resultant dry material was pulverized with a roll mill, and further classified with JIS standard sieves having mesh opening sizes of 850 μm and 106 μm, thus obtaining a water-absorbent resin powder (A) of which the major particles had particle diameters in the range of 850 to 106 μm.

The resultant water-absorbent resin powder (A) exhibited an absorption capacity of 49 (g/g) without load, and had an extractable content of 23 weight %, and a weight-average particle diameter (D50) of 330 μm wherein the ratio of particles having particle diameters of 850 to 150 μm in the water-absorbent resin powder was 97 weight %.

REFERENTIAL EXAMPLE 2

Production Example of Water-absorbent Resin Powder (B)/Neutralization Polymerization In a reactor as prepared by lidding a jacketed stainless twin-arm kneader of 10 liters in capacity with two sigma-type blades, a reaction liquid was obtained by dissolving 8.05 g of polyethylene glycol diacrylate (n=9) into 5,500 g of aqueous sodium acrylate solution having a neutralization ratio of 71 mol % (monomer concentration: 41 weight %, and average molecular weight of monomer: 87.7). Next, this reaction liquid was deaerated under an atmosphere of nitrogen for 30 minutes. Subsequently, 30.8 g of 10 weight % aqueous sodium persulfate solution and 2.57 g of 1 weight % aqueous L-ascorbic acid solution were added thereto under stirred conditions. As a result, the reaction was started after about one minute. Then, the polymerization was carried out at 20 to 95° C. while the resultant formed gel was pulverized, and the resultant crosslinked hydrogel polymer (2) was taken out after 30 minutes from the start of the polymerization.

The crosslinked hydrogel polymer (2) as obtained was in finely divided pieces having a diameter of not larger than about 5 mm. This finely divided crosslinked hydrogel polymer (2) was spread on a metal gauze with 50 mesh (a mesh opening size of 300 μm), and hot-wind-dried at 180° C. for 50 minutes. Next, the resultant dry material was pulverized with a roll mill, and further classified with a JIS standard sieve having a mesh opening size of 850 μm, thus obtaining a water-absorbent resin powder (B) of which the major particles had particle diameters in the range of not larger than 850 nm.

The resultant water-absorbent resin powder (B) exhibited an absorption capacity of 36 (g/g) without load, and had an extractable content of 10 weight %, and a weight-average particle diameter (D50) of 450 μm wherein the ratio of particles having particle diameters of 850 to 150 μm in the water-absorbent resin powder was 97 weight %.

REFERENTIAL EXAMPLE 3

Production Example of Water-absorbent Resin Powder (C)/Neutralization Polymerization A water-absorbent resin powder (C) was obtained by carrying out the same polymerization, drying, pulverization, and classification as of Referential Example 2, except that the amount of the polyethylene glycol diacrylate was changed to 5.01 g. The resultant water-absorbent resin powder (C) exhibited an absorption capacity of 39 (g/g) without load, and had an extractable content of 13 weight %, and a weight-average particle diameter (D50) of 450 μm wherein the ratio of particles having particle diameters of 850 to 150 μm in the water-absorbent resin powder was 97 weight %.

REFERENTIAL EXAMPLE 4

Production Example of Water-absorbent Resin Powder (D)/Neutralization Polymerization The polymerization, drying, and pulverization were carried out in the same way as of Referential Example 2 except that the amount of the polyethylene glycol diacrylate was changed to 5.01 g. The resultant pulverized material was further classified with JIS standard sieves having mesh opening sizes of 600 μm and 300 μm, thus obtaining a water-absorbent resin powder (D) including particles having particle diameters in the range of 600 to 300 μm. The resultant water-absorbent resin powder (D) exhibited an absorption capacity of 40 (g/g) without load, and had an extractable content of 9 weight % and a weight-average particle diameter (D50) of 450 μm.

EXAMPLE 1

Crosslinking Treatment of Water-absorbent Resin Powder (A)/in the Presence of Water-soluble Inorganic Base At first, 100 g of the water-absorbent resin powder (A) as obtained in Referential Example 1 was blended with a surface-treating agent solution which was a mixed solution comprised of: 0.027 g of ethylene glycol diglycidyl ether (Denacol EX-810, produced by Nagase Chemicals, Ltd.); 0.9 g of propylene glycol; 2.7 g of water; and 0.18 g of sodium hydrogencarbonate. Thereafter, the resultant mixture was heat-treated at 210° C. for 35 minutes, thus obtaining a water-absorbing agent (1). The resultant water-absorbing agent (I) was also powdery, and the results of the absorption capacity without load, absorption capacity under a load, and saline flow conductivity as measured were listed in Table 1.

EXAMPLE 2

Crosslinking Treatment of Water-absorbent Resin Powder (A)/in the Presence of Water-soluble Inorganic Base A water-absorbing agent (2) was obtained in the same way as of Example 1 except that 0.09 g of sodium carbonate was used instead of using the sodium hydrogencarbonate. The results of the absorption capacity without load, absorption capacity under a load, and saline flow conductivity as measured were listed in Table

COMPARATIVE EXAMPLE 1

Crosslinking Treatment of Water-absorbent Resin Powder (A)/in the Absence of Water-soluble Inorganic Base A comparative water-absorbing agent (1) was obtained in the same way as of Example 1 except that 0.81 g of isopropyl alcohol was used instead of using the sodium hydrogencarbonate. The results of the absorption capacity without load, absorption capacity under a load, and saline flow conductivity as measured were listed in Table 1.

COMPARATIVE EXAMPLE 2

Crosslinking Treatment of Water-absorbent Resin Powder (A)/in the Absence of Water-soluble Inorganic Base A comparative water-absorbing agent (2) was obtained in the same way as of Example 1 except that the sodium hydrogencarbonate was not used. The results of the absorption capacity without load, absorption capacity under a load, and saline flow conductivity as measured were listed in Table 1.

EXAMPLE 3

Crosslinking Treatment of Water-absorbent Resin Powder (B)/in the Presence of Water-soluble Inorganic Base At first, 100 g of the water-absorbent resin powder (B) as obtained in Referential Example 2 was blended with a surface-treating agent solution which was a mixed solution comprised of: 0.384 g of 1,4-butanediol; 0.6 g of propylene glycol; 3.28 g of water; and 0.3 g of 24 weight % aqueous sodium hydroxide solution (solid content: 0.072 g). Thereafter, the resultant mixture was heat-treated at 212° C. for 30 minutes, thus obtaining a water-absorbing agent (3). The resultant water-absorbing agent (3) was also in a powdery form, and the results of the absorption capacity without load, absorption capacity under a load, and saline flow conductivity as measured were listed in Table 1.

COMPARATIVE EXAMPLE 3

Crosslinking Treatment of Water-absorbent Resin Powder (B)/in the Absence of Water-soluble Inorganic Base A comparative water-absorbing agent (3) was obtained in the same way as of Example 3 except that the 24 weight % aqueous sodium hydroxide solution was not used. The results of the absorption capacity without load, absorption capacity under a load, and saline flow conductivity as measured were listed in Table 1.

EXAMPLE 4

Crosslinking Treatment of Water-absorbent Resin Powder (C)/in the Presence of Water-soluble Inorganic Base At first, 100 g of the water-absorbent resin powder (C) as obtained in Referential Example 3 was blended with a surface-treating agent solution which was a mixed solution comprised of: 0.384 g of 1,4-butanediol; 0.6 g of propylene glycol; 3.28 g of water; and 0.24 g of sodium hydrogencarbonate. Thereafter, the resultant mixture was heat-treated at 212° C. for 40 minutes, thus obtaining a water-absorbing agent (4). The resultant water-absorbing agent (4) was also in a powdery form, and the results of the absorption capacity without load, absorption capacity under a load, and saline flow conductivity as measured were listed in Table 1.

EXAMPLE 5

Crosslinking Treatment of Water-absorbent Resin Powder (C)/in the Presence of Water-soluble Inorganic Base A water-absorbing agent (5) was obtained in the same way as of Example 4 except that 0.12 g of sodium carbonate was used instead of using the sodium hydrogencarbonate. The results of the absorption capacity without load, absorption capacity under a load, and saline flow conductivity as measured were listed in Table 1.

EXAMPLE 6

Crosslinking Treatment of Water-absorbent Resin Powder (C)/in the Presence of Water-soluble Inorganic Base A water-absorbing agent (6) was obtained in the same way as of Example 4 except that 0.3 g of 24 weight % aqueous sodium hydroxide solution (solid content: 0.072 g) was used instead of using the sodium hydrogencarbonate. The results of the absorption capacity without load, absorption capacity under a load, and saline flow conductivity as measured were listed in Table 1.

COMPARATIVE EXAMPLE 4

Crosslinking Treatment of Water-absorbent Resin Powder (C)/in the Absence of Water-soluble Inorganic Base A comparative water-absorbing agent (4) was obtained in the same way as of Example 4 except that the sodium hydrogencarbonate was not used. The results of the absorption capacity without load, absorption capacity under a load, and saline flow conductivity as measured were listed in Table 1.

EXAMPLE 7

Crosslinking Treatment of Water-absorbent Resin Powder (C)/in the Presence of Water-soluble Inorganic Base A water-absorbing agent (7) was obtained in the same way as of Example 4 except that the heat-treating time was changed to 30 minutes. The results of the absorption capacity without load, absorption capacity under a load, and saline flow conductivity as measured were listed in Table 1.

EXAMPLE 8

Crosslinking Treatment of Water-absorbent Resin Powder (C)/in the Presence of Water-soluble Inorganic Base A water-absorbing agent (8) was obtained in the same way as of Example 7 except that 0.12 g of sodium carbonate was used instead of using the sodium hydrogencarbonate. The results of the absorption capacity without load, absorption capacity under a load, and saline flow conductivity as measured were listed in Table 1.

EXAMPLE 9

Crosslinking Treatment of Water-absorbent Resin Powder (C)/in the Presence of Water-soluble Inorganic Base A water-absorbing agent (9) was obtained in the same way as of Example 7 except that 0.3 g of 24 weight % aqueous sodium hydroxide solution (solid content: 0.072 g) was used instead of using the sodium hydrogencarbonate. The results of the absorption capacity without load, absorption capacity under a load, and saline flow conductivity as measured were listed in Table 1. In addition, the surface-layer extractable content of the water-absorbing agent (9) was 3.8 weight %.

COMPARATIVE EXAMPLE 5

Crosslinking Treatment of Water-absorbent Resin Powder (C)/in the Absence of Water-soluble Inorganic Base A comparative water-absorbing agent (5) was obtained in the same way as of Example 7 except that the sodium hydrogencarbonate was not used. The results of the absorption capacity without load, absorption capacity under a load, and saline flow conductivity as measured were listed in Table 1. In addition, the surface-layer extractable content of the comparative water-absorbing agent (5) was 6.5 weight %.

COMPARATIVE EXAMPLE 6

Crosslinking Treatment of Water-absorbent Resin Powder (C)/in the Absence of Water-soluble Inorganic Base A comparative water-absorbing agent (6) was obtained in the same way as of Example 9 except that 0.455 g of aluminum sulfate 14 to 18 $H_2O$ was used instead of the 24 weight % aqueous sodium hydroxide solution according to WO 00/53664. The results were listed in Table 1.

EXAMPLE 10

Crosslinking Treatment of Water-absorbent Resin Powder (C)/in the Presence of Water-soluble Inorganic Base At first, 100 g of the water-absorbent resin powder (C) as obtained in Referential Example 3 was blended with a surface-treating agent solution which was a mixed solution comprised of: 0.784 g of ethylene glycol diglycidyl ether (Denacol EX-810, produced by Nagase Chemicals, Ltd.); 4.0 g of water; and 0.5 g of 24 weight % aqueous sodium hydroxide solution (solid content: 0.12 g). Thereafter, the resultant mixture was heat-treated at 212° C. for 40 minutes, thus obtaining a water-absorbing agent (10). The resultant water-absorbing agent (10) was also in a powdery form, and the results were listed in Table 1.

COMPARATIVE EXAMPLE 7

Crosslinking Treatment of Water-absorbent Resin Powder (C)/in the Absence of Water-soluble Inorganic Base A comparative water-absorbing agent (7) was obtained in the same way as of Example 10 except that the 24 weight % aqueous sodium hydroxide solution was not used. The results were listed in Table 1.

EXAMPLE 11

Crosslinking Treatment of Water-absorbent Resin Powder (C)/in the Presence of Water-soluble Inorganic Base At first, 100 g of the water-absorbent resin powder (C) as obtained in Referential Example 3 was blended with a surface-treating agent solution which was a mixed solution comprised of: 0.4 g of 3-ethyl-3-oxetane methanol; 3.0 g of water; and 0.3 g of 24 weight % aqueous sodium hydroxide solution (solid content: 0.072 g). Thereafter, the resultant mixture was heat-treated at 212° C. for 40 minutes, thus obtaining a water-absorbing agent (11). The resultant water-absorbing agent (11) was also in a powdery form, and the results were listed in Table 1.

COMPARATIVE EXAMPLE 8

Crosslinking Treatment of Water-absorbent Resin Powder (C)/in the Absence of Water-soluble Inorganic Base A comparative water-absorbing agent (8) was obtained in the same way as of Example 11 except that the 24 weight % aqueous sodium hydroxide solution was not used. The results were listed in Table 1.

EXAMPLE 12

Crosslinking Treatment of Water-absorbent Resin Powder (C)/in the Presence of pH Buffer At first, 100 g of the water-absorbent resin powder (C) as obtained in Referential Example 3 was blended with a surface-treating agent solution which was a mixed solution comprised of: 0.15 g of ethylene glycol diglycidyl ether (Denacol EX-810, produced by Nagase Chemicals, Ltd.); 1.0 g of propylene glycol; 5.0 g of water; and 0.5 g of sodium dihydrogenphosphate dihydrate. Thereafter, the resultant mixture was heat-treated at 150° C. for 30 minutes, thus obtaining a water-absorbing agent (12). The resultant water-absorbing agent (12) was also in a powdery form, and the results were listed in Table 1.

COMPARATIVE EXAMPLE 9

Crosslinking Treatment of Water-absorbent Resin Powder (C)/in the Absence of pH Buffer A comparative water-absorbing agent (9) was obtained in the same way as of Example 12 except that the sodium dihydrogenphosphate dihydrate was not used. The results were listed in Table 1.

EXAMPLE 13

Crosslinking Treatment of Water-absorbent Resin Powder (C)/in the Presence of Water-soluble Inorganic Base A water-absorbing agent (13) was obtained in the same way as of Example 9. After the aforementioned mechanical damage had been caused to the resultant water-absorbing agent (13) for 10 minutes, the results of the absorption capacity without load, absorption capacity under a load, and saline flow conductivity of the resultant water-absorbing agent (13) as measured were listed in Table 2. Furthermore, the resultant water-absorbing agent (13) was classified with JIS standard sieves (having mesh opening sizes of 850 μm, 600 μm, 500 μm, 300 μm, and 150 μm), thus obtaining the following particles: particles (13-a) having particle diameters of smaller than 850 μm but not smaller than 600 μm; particles (13-b) having particle diameters of smaller than 600 μm but not smaller than 500 μm; particles (13-c) having particle diameters of smaller than 500 μm but not smaller than 300 μm; and particles (13-d) having particle diameters of smaller than 300 μm but not smaller than 150 μm. The results of measuring the water-absorbing agents (13-a), (13-b), (13-c), and (13-d) as obtained were listed in Table 2. In addition, the results of the SFC variation index, SFC variation coefficient, and SFC variation rate as calculated were listed in Table 3.

EXAMPLE 14

Crosslinking Treatment of Water-absorbent Resin Powder (C)/in the Presence of Water-soluble Inorganic Base A water-absorbing agent (14) was obtained in the same way as of Example 9 except that the heating time was changed to 20 minutes. After the aforementioned mechanical damage had been caused to the resultant water-absorbing agent (14) for 10 minutes, the results of the absorption capacity without load, absorption capacity under a load, and saline flow conductivity of the resultant water-absorbing agent (14) as measured were listed in Table 2. Furthermore, the resultant water-absorbing agent (14) was classified with JIS standard sieves (having mesh opening sizes of 850 μm, 600 μm, 500 μm, 300 μm, and 150 μm), thus obtaining the following particles: particles (14-a) having particle diameters of smaller than 850 μm but not smaller than 600 μm; particles (14-b) having particle diameters of smaller than 600 μm but not smaller than 500 μm; particles (14-c) having particle diameters of smaller than 500 μm but not smaller than 300 μm; and particles (14-d) having particle diameters of smaller than 300 μm but not smaller than 150 μm. The results of measuring the water-absorbing agents (14-a), (14-b), (14-c), and (14-d) as obtained were listed in Table 2. In addition, the results of the SFC variation index, SFC variation coefficient, and SFC variation rate as calculated were listed in Table 3.

COMPARATIVE EXAMPLE 10

Crosslinking Treatment of Water-absorbent Resin Powder (C)/in the Absence of Water-soluble Inorganic Base A comparative water-absorbing agent (10) was obtained in the same way as of Comparative Example 5. After the aforementioned mechanical damage had been caused to the resultant comparative water-absorbing agent (10) for 10 minutes, the results of the absorption capacity without load, absorption capacity under a load, and saline flow conductivity of the resultant comparative water-absorbing agent (10) as measured were listed in Table 2. Furthermore, the resultant comparative water-absorbing agent (10) was classified with JIS standard sieves (having mesh opening sizes of 850 μm, 600 μm, 500 μm, 300 μm, and 150 μm), thus obtaining the following particles: particles (10-a) having particle diameters of smaller than 850 μm but not smaller than 600 μm; particles (10-b) having particle diameters of smaller than 600 μm but not smaller than 500 μm; particles (10-c) having particle diameters of smaller than 500 μm but not smaller than 300 μm; and particles (10-d) having particle diameters of smaller than 300 μm but not smaller than 150 μm. The results of measuring the comparative water-absorbing agents (10-a), (10-b), (10-c), and (10-d) as obtained were listed in Table 2. In addition, the results of the SFC variation index, SFC variation coefficient, and SFC variation rate as calculated were listed in Table 3.

COMPARATIVE EXAMPLE 11

Water-absorbing Agent in Commercially Available Article

A comparative water-absorbing agent (11) was obtained by taking out a water-absorbing agent from a diaper: Pampers Active Fit that was on the market in Germany (produced by P & G and purchased on Dec. 5, 2001). The results of the absorption capacity without load, absorption capacity under a load, and saline flow conductivity of the resultant comparative water-absorbing agent (11) as measured were listed in Table 2. Furthermore, the resultant comparative water-absorbing agent (11) was classified with JIS standard sieves (having mesh opening sizes of 850 μm, 600 μm, 500 μm, 300 μm, and 150 μm), thus obtaining the following particles: particles (11-a) having particle diameters of smaller than 850 μm but not smaller than 600 μm; particles (11-b) having particle diameters of smaller than 600 μm but not smaller than 500 μm; particles (11-c) having particle diameters of smaller than 500 μm but not smaller than 300 μm; and particles (11-d) having particle diameters of smaller than 300 μm but not smaller than 150 μm. The results of measuring the comparative water-absorbing agents (11-a), (11-b), (11-c), and (11-d) as obtained were listed in Table 0.2. In addition, the results of the SFC variation index, SFC variation coefficient, and SFC variation rate as calculated were listed in Table 3.

COMPARATIVE EXAMPLE 12

Water-absorbing Agent in Commercially Available Article

A comparative water-absorbing agent (12) was obtained by taking out a water-absorbent resin from a diaper: "Pampers Sarasara Care" that was on the market in Japan (produced by P&G and purchased in December 1997). The results of the absorption capacity without load, absorption capacity under a load, and saline flow conductivity of the resultant comparative water-absorbing agent (12) as measured were listed in Table 2.

Furthermore, the resultant comparative water-absorbing agent (12) was classified with JIS standard sieves (having mesh opening sizes of 850 μm, 600 μm, 500 μm, 300 μm, and 150 μm), thus obtaining the following particles: particles (12-a) having particle diameters of smaller than 850 μm but not smaller than 600 μm; particles (12-b) having particle diameters of smaller than 600 μm but not smaller than 500 μm; particles (12-c) having particle diameters of smaller than 500 μm but not smaller than 300 μm; and particles (12-d) having particle diameters of smaller than 300 μm but not smaller than 150 μm. The results of the absorption capacity without load, absorption capacity under a load, and saline flow conductivity of the resultant comparative water-absorbing agents (12-a), (12-b), (12-c), and (12-d) as measured were listed in Table 2. In addition, the results of the SFC variation index, SFC variation coefficient, and SFC variation rate as calculated were listed in Table 3.

EXAMPLE 15

Crosslinking Treatment of Water-absorbent Resin Powder (D)/in the Presence of Water-soluble Inorganic Base At first, 100 g of the water-absorbent resin powder (D) as obtained in Referential Example 4 was blended with a surface-treating agent solution which was a mixed solution comprised of: 0.384 g of 1,4-butanediol; 0.6 g of propylene glycol; 3.28 g of water; and 0.3 g of 24 weight % aqueous sodium hydroxide solution (solid content: 0.072 g). Thereafter, the resultant mixture was heat-treated at 212° C. for 20 minutes, thus obtaining a water-absorbing agent (15). After the aforementioned mechanical damage had been caused to the resultant water-absorbing agent (15) for 10 minutes, the results of the absorption capacity without load, absorption capacity under a load, and saline flow conductivity of the resultant water-absorbing agent (15) as measured were listed in Table 2. Furthermore, the resultant water-absorbing agent (15) was classified with JIS standard sieves (having mesh opening sizes of 850 μm, 600 μm, 500 μm, 300 μm, and 150 em), thus obtaining the following particles: particles (15-b) having particle diameters of smaller than 600 μm but not smaller than 500 μm; and particles (15-c) having particle diameters of smaller than 500 μm but not smaller than 300 μm. The results of measuring the water-absorbing agents (15-b) and (15-c) as obtained were listed in Table 2. In addition, the results of the SFC variation index, SFC variation coefficient, and SFC variation rate as calculated were listed in Table 3.

EXAMPLE 16

Crosslinking Treatment of Water-absorbent Resin Powder (D)/in the Presence of Water-soluble Inorganic Base A water-absorbing agent (16) was obtained in the same way as of Example 15 except that the heating time was changed to 40 minutes. After the aforementioned mechanical damage had been caused to the resultant water-absorbing agent (16) for 10 minutes, the results of the absorption capacity without load, absorption capacity under a load, and saline flow conductivity of the resultant water-absorbing agent (16) as measured were listed in Table 2. Furthermore, the resultant water-absorbing agent (16) was classified with JIS standard sieves (having mesh opening sizes of 850 μm, 600 μm, 500 μm, 300 μm, and 150 μm), thus obtaining the following particles: particles (16-b) having particle diameters of smaller than 600 μm but not smaller than 500 μm; and particles (16-c) having particle diameters of smaller than 500 μm but not smaller than 300 μm. The results of measuring the water-absorbing agents (16-b) and (16-c) as obtained were listed in Table 2. In addition, the results of the SFC variation index, SFC variation coefficient, and SFC variation rate as calculated were listed in Table 3.

COMPARATIVE EXAMPLES 13 TO 16

Water-absorbing Agent in Commercially Available Article

As water-absorbing agents (water-absorbent resins) that were practically used, comparative water-absorbing agents (13) to (16) were obtained by taking out the water-absorbent resins from disposable diapers that were on the market in 2001. The results of the absorption capacity without load, absorption capacity under a load, and saline flow conductivity of the comparative water-absorbing agents (13) to (16) as measured were listed in Table 4.

REFERENTIAL EXAMPLE 5

Production Example of Water-absorbent Resin Powder (E)/Acid-type Polymerization and then Post-neutralization In a plastic receptacle of 2 liters, a reaction liquid was obtained by blending 252.2 g of acrylic acid, 1.1 g of N,N'-methylenebisacrylamide, and 998.4 g of water. Next, this reaction liquid was deaerated under an atmosphere of nitrogen for 30 minutes. Subsequently, 5.1 g of 2,2'-azobis(2-amidinopropane) dihydrochloride of 15 weight %, 0.63 g of 10 weight % aqueous L-ascorbic acid solution, and 3.6 g of 7 weight % aqueous hydrogen peroxide solution were added to the reaction liquid so as to start polymerization. The polymerization was carried out at 16 to 74° C., and the resultant crosslinked hydrogel polymer (5) was taken out after 3 hours from the start of the polymerization. The polymer (5) as obtained was cut into pieces about 5 cm square, and then 1,000 g of these pieces were blended with 15.0 g of 48 weight % aqueous sodium hydroxide solution in order to adjust the neutralization ratio to 65 mol %, and further the resultant mixture was passed through a meat chopper having a die diameter of 9.5 mm to obtain a finely pulverized gel. The pulverized gel as obtained was spread on a metal gauze with 50 mesh (a mesh opening size of 300 μm), and hot-wind-dried at 170° C. for 40 minutes. Next, the resultant dry material was pulverized with a roll mill, and further classified with JIS standard sieves having mesh opening sizes of 500 μm and 300 μm, thus obtaining a water-absorbent resin powder (E) of which the major particles had particle diameters in the range of 500 to 300 μm. The resultant water-absorbent resin powder (E) exhibited an absorption capacity of 49 (g/g) without load, and had an extractable content of 6 weight %.

Furthermore, in order to examine the uniformity of the neutralization ratio of the particles as obtained, 200 particles were swollen and further the neutralization index was measured by adding 0.1 weight % ethanolic solution of bromothimol blue and methyl red as a pH indicator (claim 3 in JP-A-101735/1998). As a result, as to the water-absorbent resin powders (A), (F), and (G) as obtained by the neutralization polymerization in Referential Examples 1, 6, and 7, the 200 particles were uniformly colored yellow (neutralization index: 0), while particles as variously colored from dark green to red coexisted in the particles of the water-absorbent resin powder (E), and the neutralization ratios of its individual particles were very non-uniform (neutralization index: not less than 15).

REFERENTIAL EXAMPLE 6

Production Example of Water-absorbent Resin Powder (F)/Neutralization Polymerization The polymerization, drying, and pulverization were carried out in the same way as of Referential Example 1 except that the monomer concentration, the neutralization ratio, and the amount of the polyethylene glycol diacrylate were changed into 39 weight %, 71 mol %, and 9.6 g respectively. The pulverized product as obtained was further classified with JIS standard sieves having mesh opening sizes of 500 μm and 300 μm, thus obtaining a water-absorbent resin powder (F) of which the major particles had particle diameters in the range of 500 to 300 μm. The resultant water-absorbent resin powder (F) exhibited an absorption capacity of 32 (g/g) without load, and had an extractable content of 10 weight %.

REFERENTIAL EXAMPLE 7

Production Example of Water-absorbent Resin Powder (G)/Neutralization Polymerization The polymerization, drying, and pulverization were carried out in the same way as of Referential Example 1 except that the monomer concentration, the neutralization ratio, the amount of the polyethylene glycol diacrylate, the amount of the aqueous sodium persulfate solution, the amount of the aqueous L-ascorbic acid solution, the hot-wind-drying temperature, and the hot-wind-drying time were changed into 41 weight %, 71 mol %, 5.47 g, 30.8 g, 2.57 g, 180° C., and 50 minutes respectively. The pulverized product as obtained was further classified with a JIS standard sieve having a mesh opening size of 850 μm, thus obtaining a water-absorbent resin powder (G) of which the major particles had particle diameters in the range of not larger than 850 μm.

The resultant water-absorbent resin powder (G) exhibited an absorption capacity of 38 (g/g) without load, and had an extractable content of 13 weight % and a weight-average particle diameter (D50) of 400 μm.

EXAMPLE 17

Crosslinking Treatment of Water-absorbent Resin Powder (E)/in the Presence of pH Buffer At first, 100 g of the water-absorbent resin powder (E) as obtained in Referential Example 5 was blended with a surface-treating agent solution which was a mixed solution comprised of: 0.5 g of ethylene glycol diglycidyl ether (Denacol EX-810, produced by Nagase Chemicals, Ltd.); 1.0 g of propylene glycol; 6.0 g of neutral-phosphate-salt pH standard solution (potassium dihydrogenphosphate/disodium hydrogenphosphate; pH 6.86); and 1.0 g of isopropyl alcohol. Thereafter, the resultant mixture was heat-treated at 120° C. for 30 minutes, thus obtaining a water-absorbing agent (17). The resultant water-absorbing agent (17) was also in a powdery form, and the results of the absorption capacity without load and absorption capacity under a load as measured were listed in Table 5.

COMPARATIVE EXAMPLE 17

Crosslinking Treatment of Water-absorbent Resin Powder (E)/in the Absence of pH Buffer A comparative water-absorbing agent (17) was obtained in the same way as of Example 17 except that 6.0 g of water was used instead of the neutral-phosphate-salt pH standard solution. The results of the absorption capacity without load and absorption capacity under a load as measured were listed in Table 5.

EXAMPLE 18

Crosslinking Treatment of Water-absorbent Resin Powder (F)/in the Presence of pH Buffer At first, 100 g of the water-absorbent resin powder (F) as obtained in Referential Example 6 was blended with a surface-treating agent solution which was a mixed solution comprised of: 0.32 g of 1,4-butanediol; 0.5 g of propylene glycol; 2.73 g of water; and 1.2 g of sodium dihydrogenphosphate dihydrate. Thereafter, the resultant mixture was heat-treated at 197° C. for 10 minutes, thus obtaining a water-absorbing agent (18). The resultant water-absorbing agent (18) was also in a powdery form, and the results of the absorption capacity without load and absorption capacity under a load as measured were listed in Table 5.

COMPARATIVE EXAMPLE 18

Crosslinking Treatment of Water-absorbent Resin Powder (F)/in the Absence of pH Buffer A comparative water-absorbing agent (18) was obtained in the same way as of Example 18 except that 0.6 g of phosphoric acid (85 weight %) was used instead of the sodium dihydrogenphosphate dihydrate. The results of the absorption capacity without load and absorption capacity under a load as measured were listed in Table 5.

COMPARATIVE EXAMPLE 19

Crosslinking Treatment of Water-absorbent Resin Powder (F)/in the Absence of pH Buffer A comparative water-absorbing agent (19) was obtained in the same way as of Example 18 except that the sodium dihydrogenphosphate dihydrate was not used. The results of the absorption capacity without load and absorption capacity under a load as measured were listed in Table 5.

EXAMPLE 19

Crosslinking Treatment of Water-absorbent Resin Powder (G)/in the Presence of pH Buffer At first, 100 g of the water-absorbent resin powder (G) as obtained in Referential Example 7 was blended with a surface-treating agent solution which was a mixed solution comprised of: 0.32 g of 1,4-butanediol; 0.5 g of propylene glycol; 2.73 g of water; and 0.2 g of sodium hydrogencarbonate. Thereafter, the resultant mixture was heat-treated at 212° C. for 25 minutes, thus obtaining a water-absorbing agent (19). The results of the absorption capacity without load and absorption capacity under a load as measured were listed in Table 5.

EXAMPLE 20

Crosslinking Treatment of Water-absorbent Resin Powder (G)/in the Presence of pH Buffer At first, 100 g of the water-absorbent resin powder (G) as obtained in Referential Example 7 was blended with a surface-treating agent solution which was a mixed solution comprised of: 0.32 g of 1,4-butanediol; 0.5 g of propylene glycol; 2.73 g of water; and 0.24 g of potassium hydrogencarbonate. Thereafter, the resultant mixture was heat-treated at 212° C. for 25 minutes, thus obtaining a water-absorbing agent (20). The results of the absorption capacity without load and absorption capacity under a load as measured were listed in Table 5.

COMPARATIVE EXAMPLE 20

Crosslinking Treatment of Water-absorbent Resin Powder (G)/in the Absence of pH Buffer A comparative water-absorbing agent (20) was obtained in the same way as of Example 19 except that the sodium hydrogencarbonate was not used. The results of the absorption capacity without load and absorption capacity under a load as measured were listed in Table 5.

EXAMPLE 21

Continuous Production System

The aqueous solution polymerization (belt residence time: about 30 minutes, and thickness: about 25 mm) of partial sodium salt of acrylic acid having a neutralization ratio of 71 mol % and polyethylene glycol diacrylate (n=9) was continuously carried out in the ratio as described in Referential Example 3. The crosslinked hydrogel polymer of the resultant water-absorbent resin was roughly pulverized into particles with a meat chopper, and then the pulverized gel as obtained was spread thin and put on a porous plate of a band dryer and continuously hot-wind-dried at 180° C. for 30 minutes. A block-shaped dry polymer was obtained at an outlet of the dryer. This dry polymer was taken out and, simultaneously therewith, disintegrated, and the particulate dry material as obtained was pulverized by continuously supplying it to a three-stage roll granulator (roll setting gap: 1.0 mm/0.55 mm/0.42 mm in order from the top) at a rate of 1,000 kg/h. The resultant particulate water-absorbent resin powder having a temperature of about 60° C. was classified with a sieving machine having a metal gauze with a mesh opening size of 850 μm, thus obtaining a water-absorbent resin powder (H) including particles having particle diameters of smaller than 850 μm but not smaller than 150 μm in a ratio of not less than 90 weight % (average particle diameter: 430 to 460 μm). The resultant water-absorbent resin powder (H) exhibited an average absorption capacity of 40 (g/g) without load (CRC), and had an average extractable content of 11 weight %. Incidentally, the CRC and extractable content are average of values as measured every 2 hours (2,000 kg/lot).

Furthermore, the water-absorbent resin powder (H) was continuously supplied to a high-speed continuous blender (Turbulizer/1,000 rpm) at a rate of 1,000 kg/h, and then was spraywise blended with an aqueous surface-crosslinking agent solution including 1,4-butanediol, propylene glycol, water, and a 24% aqueous sodium hydroxide solution in ratios of 0.384, 0.63, 3.39, and 0.3 (weight % relative to powder) respectively by a spray which could form liquid drops of about 200 μm. Subsequently, the resultant mixture was continuously heat-treated at 195° C. for 40 minutes with a paddle dryer, thus obtaining a water-absorbing agent powder. The resultant water-absorbing agent powder was further classified with a sieving machine having a metal gauze with a mesh opening size of 850 μm, thus obtaining a water-absorbing agent (21) including particles having particle diameters of smaller than 850 μm but not smaller than 150 μm in a ratio of not less than 90 weight %.

The aforementioned successive steps (polymerization, drying, pulverization, and heat treatment) were continuously carried out for 24 hours, and the properties of the water-absorbing agent (number of lots: 11 lots) were measured every 2 hours (2,000 kg/lot). As a result, the average of the absorption capacities without load was 31.1 g/g, and the average of the absorption capacities under a load was 25.5 g/g, and the average of the saline flow conductivities was 30 (SFC values of individual lots: 32, 32, 28, 28, 30, 27, 27, 32, 31, 32, and 28), and the standard deviation value of the SFC was 2.1.

EXAMPLE 22

Continuous Production System

A water-absorbing agent (22) was obtained by carrying out a continuous production in the same way as of Example 21 except for changing the 24 hours to 10 days. Then, the properties of the water-absorbing agent (number of lots: 110 lots) were measured every 2 hours (2,000 kg/lot). As a result, the average of the absorption capacities without load was 31.3 g/g, and the average of the absorption capacities under a load was 25.2 g/g, and the average of the saline flow conductivities was 30 (SFC values of individual lots were omitted.), and the standard deviation value of the SFC was 3.9.

COMPARATIVE EXAMPLE 21

Continuous Production System

A comparative water-absorbing agent (21) was obtained by carrying out a continuous production in the same way as of Example 21 except that the 24% aqueous sodium hydroxide solution was not used. Then, the properties of the water-absorbing agent (number of lots: 11 lots) were measured every 2 hours (2,000 kg/lot). As a result, the average of the absorption capacities without load was 31.1 g/g, and the average of the absorption capacities under a load was 24.2 g/g, and the average of the saline flow conductivities was 20 (SFC values of individual lots: 26, 17, 11, 17, 17, 18, 20, 17, 16, 28, and 28), and the standard deviation value of the SFC was 5.5.

The water-absorbing agents (21) and (22) as described in Examples 21 and 22 have smaller standard deviations of SFC than the comparative water-absorbing agent (21) as described in Comparative Example 21. When the water-absorbing agent according to the present invention is continuously produced, it shows that articles having poor qualities (such as articles having a low SFC) are not caused and the scatter of the quality (SFC) is lowered.

TABLE 1

| | Water-absorbent resin powder as used | Additive (weight %: based on water-absorbent resin powder) | Absorption capacity without load (g/g) | Absorption capacity under a load (g/g) | Saline flow conductivity (SFC) ($10^{-7} \times cm^3 \times s \times g^{-1}$) |
|---|---|---|---|---|---|
| Example 1 | (A) | Sodium hydrogencarbonate (0.18) | 38.2 | 25.1 | 15 |
| Example 2 | ↑ | Sodium carbonate (0.09) | 37.6 | 25.0 | 14 |
| Comparative Example 1 | ↑ | Isopropyl alcohol (0.12) | 39.4 | 21.8 | 11 |
| Comparative Example 2 | ↑ | None | 38.5 | 21.5 | 10 |
| Example 3 | (B) | 24 weight % aqueous sodium hydroxide solution (0.3) | 29.5 | 25.3 | 45 |

TABLE 1-continued

| | Water-absorbent resin powder as used | Additive (weight %: based on water-absorbent resin powder) | Absorption capacity without load (g/g) | Absorption capacity under a load (g/g) | Saline flow conductivity (SFC) ($10^{-7} \times cm^3 \times s \times g^{-1}$) |
|---|---|---|---|---|---|
| Comparative Example 3 | ↑ | None | 29.5 | 24.5 | 35 |
| Example 4 | (C) | Sodium hydrogencarbonate (0.24) | 29.6 | 23.3 | 55 |
| Example 5 | ↑ | Sodium carbonate (0.12) | 29.7 | 23.5 | 53 |
| Example 6 | ↑ | 24 weight % aqueous sodium hydroxide solution (0.3) | 29.3 | 23.6 | 58 |
| Comparative Example 4 | ↑ | None | 29.6 | 23.7 | 38 |
| Example 7 | ↑ | Sodium hydrogencarbonate (0.24) | 31.9 | 25.8 | 41 |
| Example 8 | ↑ | Sodium carbonate (0.12) | 31.4 | 25.0 | 43 |
| Example 9 | ↑ | 24 weight % aqueous sodium hydroxide solution (0.3) | 31.2 | 25.6 | 45 |
| Comparative Example 5 | ↑ | None | 31.5 | 25.2 | 28 |
| Comparative Example 6 | ↑ | Aluminum sulfate 14 to 18 $H_2O$ | 31.8 | 22.7 | 30 |
| Example 10 | ↑ | 24 weight % aqueous sodium hydroxide solution (0.3) | 31.6 | 25.1 | 38 |
| Comparative Example 7 | ↑ | None | 31.4 | 25.2 | 26 |
| Example 11 | ↑ | 24 weight % aqueous sodium hydroxide solution (0.3) | 31.6 | 25.0 | 41 |
| Comparative Example 8 | ↑ | None | 31.5 | 25.0 | 25 |
| Example 12 | ↑ | 24 weight % aqueous sodium hydroxide solution (0.3) | 31.5 | 25.8 | 41 |
| Comparative Example 9 | ↑ | None | 31.3 | 24.0 | 29 |

Note)
Every water-absorbing agent and comparative water-absorbing agent as listed above included particles having particle diameters of 850 to 150 μm in a ratio of not less than 95 weight %, and had an average particle diameter in the range of 300 to 500 μm and a bulk density in the range of 0.60 to 0.73 g/ml.

TABLE 2

| Water-absorbing agent as measured | Absorption capacity without load (g/g) | Absorption capacity under a load (g/g) | Saline flow conductivity (SFC) ($10^{-7} \times cm^3 \times s \times g^{-1}$) | Particle diameter distribution (weight %) |
|---|---|---|---|---|
| Example 13 | | | | |
| (13-a) | 33.2 | 26.5 | 35 | 21 |
| (13-b) | 32.8 | 26.7 | 37 | 22 |
| (13-c) | 30.8 | 26.4 | 39 | 35 |
| (13-d) | 25.8 | 23.9 | 47 | 17 |
| Water-absorbing agent (13) | 31.7 | 25.8 | 42 | 95 |
| Example 14 | | | | |
| (14-a) | 34.0 | 25.9 | 18 | 22 |
| (14-b) | 34.3 | 26.7 | 21 | 23 |
| (14-c) | 32.3 | 26.4 | 24 | 32 |
| (14-d) | 26.5 | 23.7 | 26 | 18 |
| Water-absorbing agent (14) | 33.1 | 24.2 | 20 | 95 |
| Comparative Example 10 | | | | |
| (10-a) | 33.9 | 26.5 | 18 | 21 |
| (10-b) | 33.7 | 26.9 | 29 | 23 |
| (10-c) | 31.9 | 26.8 | 36 | 34 |
| (10-d) | 26.6 | 24.0 | 38 | 18 |
| Comparative water-absorbing agent (10) | 31.9 | 25.8 | 30 | 96 |
| Comparative Example 11 | | | | |
| (11-a) | 31.5 | 23.5 | 15 | 24 |
| (11-b) | 31.4 | 23.3 | 20 | 28 |
| (11-c) | 30.1 | 23.2 | 18 | 33 |
| (11-d) | 26.5 | 20.9 | 9 | 12 |

TABLE 2-continued

| Water-absorbing agent as measured | Absorption capacity without load (g/g) | Absorption capacity under a load (g/g) | Saline flow conductivity (SFC) ($10^{-7} \times cm^3 \times s \times g^{-1}$) | Particle diameter distribution (weight %) |
|---|---|---|---|---|
| Comparative water-absorbing agent (11) Comparative Example 12 | 30.1 | 22.2 | 11 | 97 |
| (12-a) | 29.9 | 22.7 | 18 | 14 |
| (12-b) | 30.6 | 23.8 | 15 | 26 |
| (12-c) | 29.9 | 23.2 | 10 | 38 |
| (12-d) | 26.7 | 22.5 | 9 | 20 |
| Comparative water-absorbing agent (12) Example 15 | 29.7 | 21.4 | 6 | 98 |
| (15-a) | — | — | — | — |
| (15-b) | 35.5 | 26.9 | 21 | 35 |
| (15-c) | 34.6 | 26.8 | 20 | 65 |
| (15-d) | — | — | — | — |
| Water-absorbing agent (15) Example 16 | 35.0 | 26.9 | 20 | 100 |
| (16-a) | — | — | — | — |
| (16-b) | 32.5 | 26.2 | 55 | 32 |
| (16-c) | 31.9 | 26.3 | 51 | 68 |
| (16-d) | — | — | — | — |
| Water-absorbing agent (16) | 32.1 | 26.3 | 50 | 100 |

Note)
The particle diameter distributions of the water-absorbing agents (13) to (16) and comparative water-absorbing agents (10) to (12) show ratios (weight %) of particles having particle diameters of smaller than 850 μm but not smaller than 150 μm.

TABLE 3

|  | SFC variation index (%) | SFC variation coefficient | SFC variation rate |
|---|---|---|---|
| Example 13 | 12.5 | 0.13 | 0.74 |
| Example 14 | 17.5 | 0.16 | 0.69 |
| Comparative Example 10 | 30.1 | 0.30 | 0.47 |
| Comparative Example 11 | 43.6 | 0.31 | 0.45 |
| Comparative Example 12 | 70.7 | 0.33 | 0.50 |

TABLE 3-continued

|  | SFC variation index (%) | SFC variation coefficient | SFC variation rate |
|---|---|---|---|
| Example 15 | 3.5 | 0.03 | 0.95 |
| Example 16 | 5.7 | 0.05 | 0.93 |

The water-absorbing agents (1) and (2) as described in Examples 1 and 2 have larger absorption capacities under a load, and are more excellent in balance of absorption capacities without load and the absorption capacities under a load, than the comparative water-absorbing agents (1) and (2) which are similarly surface-crosslinked.

The water-absorbing agent (3) as described in Example 3 is more excellent in balance of three properties than the comparative water-absorbing agent (3) as described in Comparative Example 3, wherein the three properties are an absorption capacity without load, an absorption capacity under a load, and a saline flow conductivity.

Furthermore, the water-absorbing agents (4), (5) and (6) as described in Examples 4, 5, and 6 display nearly as large absorption capacities without load as the comparative water-absorbing agent (4) as described in Comparative Example 4, but display higher saline flow conductivity values.

Similarly, also as to the water-absorbing agents (7), (8) and (9) as described in Examples 7, 8, and 9, they display nearly as large absorption capacities without load as the comparative water-absorbing agents (5) and (6) as described in Comparative Examples 5 and 6, but display higher absorption capacity values under a load and saline flow conductivity values.

In addition, the water-absorbing agents (10), (11) and (12) as described in Examples 10, 11, and 12 respectively display nearly as large absorption capacities without load as the comparative water-absorbing agents (7), (8), and (9) as described in Comparative Examples 7, 8, and 9, but display higher saline flow conductivity values.

The water-absorbing agents (13) and (14) as described in Examples 13 and 14 have smaller SFC variation indices and SFC variation coefficients, and larger SFC variation rates than the comparative water-absorbing agents (10), (11), and (12) as described in Comparative Examples 10, 11, and 12, and every scatter of the SFC is lowered.

In addition, the water-absorbing agents (15) and (16) as described in Examples 15 and 16 also have small SFC variation indices and SFC variation coefficients, and large SFC variation rates, and every scatter of the SFC is lowered.

In this way, the water-absorbing agent as produced by the process according to the present invention is excellent in balance of three properties that are an absorption capacity without load, an absorption capacity under a load, and a saline flow conductivity, and has good performance. Furthermore, the water-absorbing agent is a very excellent water-absorbing agent in stabilizing properties of diapers because the scatter of the SFCs according to particle diameters is lowered.

TABLE 4

|  | Maker | Diaper name | Date of purchase | Lot. No | Absorption capacity without load (g/g) | Absorption capacity under a load (g/g) | Saline flow conductivity (SFC) ($10^{-7} \times cm^3 \times s \times g^{-1}$) |
|---|---|---|---|---|---|---|---|
| Comparative Example 13 | Kimberly-Clark | HUGGIES overnight | July 2001 | DP026305B15 | 29.0 | 16.0 | 1 |
| Comparative Example 14 | Kimberly-Clark | HUGGIES Freedom | August 2001 | 07/2002 16220701022 | 30.0 | 19.0 | 1 |
| Comparative Example 15 | ARQUEST | SUPREME | June 2001 | 0201NS | 31.0 | 22.0 | 5 |

TABLE 4-continued

|  | Maker | Diaper name | Date of purchase | Lot. No | Absorption capacity without load (g/g) | Absorption capacity under a load (g/g) | Saline flow conductivity (SFC) ($10^{-7} \times cm^3 \times s \times g^{-1}$) |
|---|---|---|---|---|---|---|---|
| Comparative Example 16 | Uni-charm Corporation | Mammy poco Cotton Permeable sheet | December 2001 | 12037232 | 33.0 | 19.0 | 0 |

All the comparative water-absorbing agents (13), (14), (15), and (16) as described in Comparative Examples 13, 14, 15, and 16 are poor in balance of three properties which are an absorption capacity without load, an absorption capacity under a load, and a saline flow conductivity.

TABLE 5

|  | Water-absorbent resin powder as used | Additive (weight %: based on water-absorbent resin powder) | Absorption capacity without load (g/g) | Absorption capacity under a load (g/g) | Total of absorption capacities without load and under a load (g/g) |
|---|---|---|---|---|---|
| Example 17 | (D) | Sodium phosphate (6.0) | 36 | 26 | 62 |
| Comparative Example 17 | ↑ | None | 39 | 17 | 56 |
| Example 18 | (E) | Sodium dihydrogenphosphate (1.2) | 28 | 23 | 51 |
| Comparative Example 18 | ↑ | Phosphoric acid (1.2) | 28 | 21 | 49 |
| Comparative Example 19 | ↑ | None | 30 | 18 | 48 |
| Example 19 | (F) | Sodium hydrogencarbonate (0.2) | 32 | 25 | 57 |
| Example 20 | ↑ | Potassium hydrogencarbonate (0.24) | 32 | 25 | 57 |
| Comparative Example 20 | ↑ | None | 32 | 23 | 55 |

Note)
Every water-absorbing agent and comparative water-absorbing agent as listed above included particles having particle diameters of 850 to 150 μm in a ratio of not less than 95 weight %, and had an average particle diameter in the range of 300 to 500 μm and a bulk density in the range of 0.60 to 0.73 g/ml.

The water-absorbing agent (17) as described in Example 17 has a larger absorption capacity under a load, and is more excellent in balance of the absorption capacity without load and the absorption capacity under a load and in the total thereof, than the comparative water-absorbing agent (17) as described in Comparative Example 17.

In addition, in the case of the water-absorbing agent (18) as described in Example 18 in comparison with the comparative water-absorbing agent (18) as described in Comparative Example 18 to which the phosphoric acid had been added, the crosslinking reaction similarly proceeds in a short time of 10 minutes, and the absorption capacity value without load is equal, but a higher absorption capacity value under a load is displayed. Furthermore, as to the comparative water-absorbing agent (19) as described in Comparative Example 19 to which nothing had been added, the crosslinking reaction does not proceed sufficiently in a short time of 10 minutes, and the lowering of the absorption capacity without load is hardly observed, and the absorption capacity under a load is also low.

In this way, the water-absorbing agent as produced by the process according to the present invention is excellent in balance of an absorption capacity without load and an absorption capacity under a load and in the total thereof, and has good performance even in a short reaction time.

Various details of the invention may be changed without departing from its spirit not its scope. Furthermore, the foregoing description of the preferred embodiments according to the present invention is provided for the purpose of illustration only, and not for the purpose of limiting the invention as defined by the appended claims and their equivalents.

INDUSTRIAL APPLICATION

The present invention can provide: a process for producing a water-absorbing agent in a short time; and a water-absorbing agent; which process involves, in the crosslinking treatment step, the use of an additive that displays effects as a blending promoter but never inhibits a crosslinking reaction and, according to circumstances, further has effects as a reaction catalyst, and which process can achieve uniform surface-crosslinking almost regardless of the difference in neutralization ratio of a water-absorbent resin resultant from partial-neutralization polymerization and almost regardless of the uniformity of the neutralization ratio resultant from the post-neutralization operation after the acid-type polymerization, and therefore can give a water-absorbing agent that is excellent in balance of absorption capacity without load, absorption capacity under load, and saline flow conductivity and further exhibits so little scatter of the saline flow conductivity values among lots or in each lot during the production as to have stable properties.

The invention claimed is:

1. A water-absorbing agent, which is a particulate water-absorbing agent of which the major proportion is comprised of a water-absorbent resin that is obtained by a process including the step of polymerizing an unsaturated monomer component and has a crosslinked structure,
   where the particulate water-absorbing agent includes particles having particle diameters of smaller than 850 μm but not smaller than 150 μm in an amount of not less than 90 weight % of all particles of the particulate water-absorbing agent; and where the particles include at least two members selected from the group consisting of: particles (A1) having particle diameters of smaller than 850 μm but not smaller than 600 μm; particles (A2) having particle diameters of smaller than 600 μm but not smaller than 500 μm; particles (A3) having particle diameters of smaller than 500 μm but not smaller than 300 μm; and particles (A4) having particle diameters of smaller than 300 μm but not smaller than 150 μm; and where the water-absorbing agent further has the following properties:
   a 30-minute absorption capacity of not less than 31 g/g without load for a 0.90 weight % physiological saline (CRC);
   a 60-minute absorption capacity of not less than 24 g/g under a load of 4.83 kPa for a 0.90 weight % physiological saline (AAP);
   a saline flow conductivity of not less than 20 (unit: $10^{-7} \times cm^3 \times s \times g^{-1}$) for a 0.69 weight % physiological saline (SFC); and
   an SFC variation index of 0 to 25% wherein the SFC variation index is defined by the following equation (1):

$$SFC \text{ variation index } (\%) = [(\text{standard deviation of } SFCs \text{ of particles } A1 \text{ to } A4)/(SFC \text{ of entire particulate water-absorbing agent})] \times 100 \quad (1).$$

2. A water-absorbing agent according to claim 1, wherein said water-absorbing agent comprises particles A1, A2, A3 and A4, each being present in an amount of not less than 0.1 weight % respectively.

3. A water-absorbing agent according to claim 1, which has an SFC variation coefficient of 0 to 0.25, wherein the SFC variation coefficient is defined by the following equation (2):

$$SFC \text{ variation coefficient} = (\text{standard deviation of } SFCs \text{ of particles } A1 \text{ to } A4)/(\text{average of } SFCs \text{ of particles } A1 \text{ to } A4) \quad (2).$$

4. A water-absorbing agent according to claim 1, which has an SFC variation rate of 0.65 to 1.00, wherein the SFC variation rate is defined by the following equation (3):

$$SFC \text{ variation rate} = (\text{minimum } SFC \text{ among } SFCs \text{ of particles } A1 \text{ to } A4)/(\text{maximum } SFC \text{ among } SFCs \text{ of particles } A1 \text{ to } A4) \quad (3).$$

5. A water-absorbing agent according to claim 1, which further comprises a cationic polymer compound and/or a water-insoluble fine particle.

6. A water-absorbing agent, which is a particulate water-absorbing agent of which the major proportion is comprised of a water-absorbent resin that is obtained by a process including the step of polymerizing an unsaturated monomer component and has a crosslinked structure,
   where the particulate water-absorbing agent includes particles having particle diameters of smaller than 850 μm but not smaller than 150 μm in an amount of not less than 90 weight % of all particles of the particulate water-absorbing agent; and where the particles include at least two members selected from the group consisting of: particles (A1) having smaller than 850 μm but not smaller than 600 μm; particles (A2) having particle diameters of smaller than 600 μm but not smaller than 500 μm; particles (A3) having particle diameters of smaller than 500 μm but not smaller than 300 μm; and particles (A4) having particle diameters of smaller than 300 μm but not smaller than 150 μm; and where said water-absorbing agent further has the following properties:
   a 30-minute absorption capacity of not less than 31 g/g without load for a 0.90 weight % physiological saline (CRC);
   a 60-minute absorption capacity of not less than 24 g/g under a load of 4.83 kPa for a 0.90 weight % physiological saline (AAP);
   a saline flow conductivity of not less than 20 (unit: $10^{-7} \times cm^3 \times s \times g^{-1}$) for a 0.69 weight % physiological saline (SFC); and
   an SFC variation coefficient of 0 to 0.25, wherein the SFC variation coefficient is defined by the following equation (2):

$$SFC \text{ variation coefficient} = (\text{standard deviation of } SFCs \text{ of particles } A1 \text{ to } A4)/(\text{average of } SFCs \text{ of particles } A1 \text{ to } A4) \quad (2).$$

7. A continuously produced water-absorbing agent, which is a particulate water-absorbing agent of which the major proportion is comprised of a water-absorbent resin that is obtained by a process including the step of polymerizing an unsaturated monomer component and has a crosslinked structure,
   where the particulate water-absorbing agent includes particles having particle diameters of smaller than 850 μm but not smaller than 150 μm in an amount of not less than 90 weight % of all particles of the particulate water-absorbing agent; and where the particles include at least two members selected from the group consisting of: particles (A1) having particle diameters of smaller than 850 μm but not smaller than 600 μm; particles (A2) having particle diameters of smaller than 600 μm but not smaller than 500 μm; particles (A3) having particle diameters of smaller than 500 μm but not smaller than 300 μm; and particles (A4) having particle diameters of smaller than 300 μm but not smaller than 150 μm; and where the water-absorbing agent further has the following properties:
   a 30-minute absorption capacity of not less than 31 g/g without load for a 0.90 weight % physiological saline (CRC);
   a 60-minute absorption capacity of not less than 24 g/g under a load of 4.83 kPa for a 0.90 weight % physiological saline (AAP);

a saline flow conductivity of not less than 20 (unit: $10^{-7} \times cm^3 \times s \times g^{-1}$) for a 0.69 weight % physiological saline (SEC); and an SFC standard deviation of not more than 5.0 in a continuous production system, wherein the SFC standard deviation in a continuous production system is defined by the following equation (4):

$$SFC \text{ standard deviation in a continuous production system} = \text{standard deviation of } SEC \text{ of each lot} \quad (4)$$

where: the CRC, AAP, and SEC are on average of the lots; each lot has a weight of not less than 20 kg; and the number of the lots is not smaller than 10.

8. A water-absorbing agent, which is a particulate water-absorbing agent obtained by a process including the steps of: polymerizing a monomer including an acid-group-containing monomer (salt); and then post-neutralizing the resultant polymer; and then surface-crosslinking the resultant water-absorbent resin, where the particulate water-absorbing agent or the water-absorbent resin has a neutralization index of not less than 15 and exhibits a 60 minutes' absorption capacity of not less than 20 g/g under a load of 4.83 kPa for a 0.90 weight % physiological saline (AAP) after the surface-crosslinking.

9. A water-absorbing agent, which is obtained by a production process comprising the step of blending a water-absorbent resin powder (a) with a noncrosslinkable water-soluble inorganic base (b1) and/or an irreducible alkaline-metal-salt pH buffer (b2) and further with a dehydratable crosslinking agent (c1), thereby subjecting the water-absorbent resin powder (a) to crosslinking treatment, wherein the water-absorbent resin powder (a) contains an acid group, and wherein the dehydratable crosslinking agent (c1) is reactable with the acid group.

10. A sanitary material, which comprises the water-absorbing agent as recited in claim 1.

11. A sanitary material, which comprises the water-absorbing agent as recited in claim 6.

12. A sanitary material, which comprises the water-absorbing agent as recited in claim 7.

13. A sanitary material, which comprises the water-absorbing agent as recited in claim 8.

14. A sanitary material, which comprises the water-absorbing agent as recited in claim 9.

15. A water-absorbing agent according to claim 9, wherein the water-soluble inorganic base (b1) is at least one member selected from the group consisting of alkaline metal salts, ammonium salts, alkaline metal hydroxides, and ammonia or its hydroxide.

16. A water-absorbing agent according to claim 9, wherein the pH buffer (b2) is an inorganic salt comprised of a weak acid and a strong base.

17. A water-absorbing agent according to claim 9, wherein the pH buffer (b2) is a partially alkaline-metal-neutralized salt of a polybasic acid.

18. A water-absorbing agent according to claim 9, wherein the dehydratable crosslinking agent (c1) is a polyhydric alcohol compound.

* * * * *

UNITED STATES PATENT AND TRADEMARK OFFICE
CERTIFICATE OF CORRECTION

PATENT NO. : 7,312,278 B2  Page 1 of 1
APPLICATION NO. : 10/333614
DATED : December 25, 2007
INVENTOR(S) : Yasuhisa Nakashima et al.

It is certified that error appears in the above-identified patent and that said Letters Patent is hereby corrected as shown below:

On the Title Page,

Insert Item (30)   Foreign Application Priority Data

Jun. 8, 2001   JAPAN..................2001-173392
Jun. 8, 2001   JAPAN..................2001-173417

Signed and Sealed this

Third Day of June, 2008

JON W. DUDAS
*Director of the United States Patent and Trademark Office*